(12) United States Patent
Short et al.

(10) Patent No.: US 12,344,570 B2
(45) Date of Patent: ***Jul. 1, 2025

(54) AMINOTETRALINE ACTIVATORS OF SEROTONIN RECEPTORS

(71) Applicant: Atai Therapeutics, Inc., New York, NY (US)

(72) Inventors: Glenn Short, Scituate, MA (US); Robert B. Perni, Marlborough, MA (US); Tanweer A. Khan, Bridgewater, NJ (US)

(73) Assignee: Atai Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,711

(22) Filed: Aug. 23, 2023

(65) Prior Publication Data

US 2024/0300885 A1    Sep. 12, 2024

Related U.S. Application Data

(63) Continuation of application No. 18/146,785, filed on Dec. 27, 2022, now Pat. No. 11,827,580.

(60) Provisional application No. 63/294,030, filed on Dec. 27, 2021.

(51) Int. Cl.
*C07C 211/42*     (2006.01)
*C07D 217/08*     (2006.01)

(52) U.S. Cl.
CPC .......... *C07C 211/42* (2013.01); *C07D 217/08* (2013.01)

(58) Field of Classification Search
CPC .............................. C07C 211/42; C07D 217/08
See application file for complete search history.

(56) References Cited

U.S. PATENT DOCUMENTS

| | | | |
|---|---|---|---|
| 4,239,903 A * | 12/1980 | Isoda | C07D 317/70 560/70 |
| 5,807,897 A | 9/1998 | Warawa et al. | |
| 6,201,025 B1 | 3/2001 | Dax et al. | |
| 6,225,352 B1 | 5/2001 | Horwell et al. | |
| 9,101,613 B2 | 8/2015 | Laudon et al. | |
| 9,720,005 B2 | 8/2017 | McConnell et al. | |
| 10,703,711 B2 | 7/2020 | Singh et al. | |
| 11,306,059 B2 | 4/2022 | Weeber et al. | |
| 11,629,127 B2 | 4/2023 | Weeber et al. | |
| 11,827,580 B2 * | 11/2023 | Short | C07C 381/10 |
| 11,827,582 B2 | 11/2023 | Singh et al. | |
| 11,962,574 B2 | 3/2024 | Short et al. | |
| 2002/0115715 A1 | 8/2002 | Dax et al. | |
| 2003/0079301 A1 | 5/2003 | Sauter et al. | |
| 2003/0199497 A1 | 10/2003 | Ruat et al. | |
| 2005/0152858 A1 | 7/2005 | Bertz et al. | |
| 2007/0099909 A1 | 5/2007 | Chen et al. | |
| 2007/0196395 A1 | 8/2007 | Mackerell et al. | |
| 2008/0248511 A1 | 10/2008 | Daily et al. | |
| 2008/0318957 A1 | 12/2008 | Glinka et al. | |
| 2009/0275563 A1 | 11/2009 | Bonaventure | |
| 2010/0113539 A1 | 5/2010 | Scott et al. | |
| 2010/0130742 A1 | 5/2010 | Harris et al. | |

(Continued)

FOREIGN PATENT DOCUMENTS

| | | |
|---|---|---|
| EP | 0883599 B1 | 6/2002 |
| JP | 2023531311 A | 7/2023 |

(Continued)

OTHER PUBLICATIONS

Alves de Barros et al., "Synthesis of 25X-BOMes and 25X-NBOHs (X = H, I, Br) for pharmacological studies and as reference standards for forensic purposes," Tetrahedron Letters (2021), 66, 152804 4 pages.

(Continued)

*Primary Examiner* — Timothy R Rozof
(74) *Attorney, Agent, or Firm* — COOLEY LLP

(57) ABSTRACT

Provided herein are compounds of Formula (I), (I-A), (I-B), (II), (II-A), (II-B), (III), (III-A), (IV), and (IV-A), or pharmaceutically acceptable salt thereof described herein. Also provided herein are pharmaceutical compositions comprising a compound Formula (I), (I-A), (I-B), (II), (II-A), (II-B), (III), (III-A), (IV), and (IV-A), or pharmaceutically acceptable salt thereof, and methods of using a compound of Formula (I), (I-A), (I-B), (II), (II-A), (II-B), (III), (III-A), (IV), and (IV-A), or pharmaceutically acceptable salt thereof, e.g., in the treatment of a mental health disease or disorder.

18 Claims, 2 Drawing Sheets

(56) References Cited

U.S. PATENT DOCUMENTS

| | | |
|---|---|---|
| 2012/0028995 A1 | 2/2012 | Ansorge et al. |
| 2012/0283298 A1 | 11/2012 | Crider et al. |
| 2015/0346226 A1 | 12/2015 | McConnell et al. |
| 2019/0315689 A1 | 10/2019 | Chen et al. |
| 2020/0325124 A1 | 10/2020 | Lavoie et al. |
| 2021/0052519 A1 | 2/2021 | Singh et al. |
| 2021/0145851 A1 | 5/2021 | Stamets |
| 2021/0315860 A1 | 10/2021 | Hopkins et al. |
| 2021/0403425 A1 | 12/2021 | Bryson |
| 2023/0138118 A1 | 5/2023 | Short et al. |
| 2023/0202965 A1 | 6/2023 | Short et al. |
| 2023/0331658 A1 | 10/2023 | Singh et al. |
| 2024/0254087 A1 | 8/2024 | Wallach et al. |
| 2024/0294461 A1 | 9/2024 | Short et al. |
| 2024/0366531 A1 | 11/2024 | Bowen et al. |
| 2024/0366542 A1 | 11/2024 | Khan et al. |

FOREIGN PATENT DOCUMENTS

| | | |
|---|---|---|
| WO | WO 9323364 A1 | 11/1993 |
| WO | WO-2019084338 A1 | 5/2019 |
| WO | WO-2019089066 A1 | 5/2019 |
| WO | WO 2020037372 A1 | 2/2020 |
| WO | WO-2021025723 A1 | 2/2021 |
| WO | WO-2022006186 A1 | 1/2022 |
| WO | WO-2022212854 A1 | 10/2022 |
| WO | WO-2022241006 A1 | 11/2022 |
| WO | WO 2022261240 A2 | 12/2022 |
| WO | WO-2022261263 A1 | 12/2022 |
| WO | WO-2023114320 A1 | 6/2023 |
| WO | WO-2023129909 A1 | 7/2023 |
| WO | WO-2024124056 A1 | 6/2024 |
| WO | WO-2024138032 A1 | 6/2024 |
| WO | WO-2024138041 A1 | 6/2024 |
| WO | WO-2024192150 A2 | 9/2024 |
| WO | WO-2024229149 A1 | 11/2024 |

OTHER PUBLICATIONS

Baker et al., "Neurochemical and neuropharmacological investigation of Ncyanoethyltryptamine, a potential prodrug of tryptamine," Proc West Pharmacol Soc., 1987;30:307-11.

Benneyworth et al., Complex discriminative stimulus properties of (+) lysergic acid diethylamide (LSD) in C57B1/6J mice, Psychopharmacology, Jun. 2005, pp. 854-862.

Carter et al., Modulating the rate and rhythmicity of perceptual rivalry alternations with the mixed 5-HT2A and 5-HT1A agonist psilocybin, Neuropsychopharmacology, Jun. 2005, pp. 1154-1162.

CAS Registry No. 1152718-19-8, Benzenemethanamine, N-[4-(1, 1-dimethylethyl)cyclohexyl]-2,4- difluoro-a-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1, 1-dimethylpropyl)cyclohexyl]-2,5-difluoro-, Jun. 9, 2009, 1 page.

CAS Registry No. 127456-43-3, Phenol, 2-[[[4-(1, 1-dimethylethyl)cyclohexyl]amino]methyl]-4-(1, 1-dimethylpropyl)-, trans- (9C1), Jun. 1, 1990, 1 page.

CAS Registry No. 127456-44-4, 1H-Inden-5-ol, 6-[[[4-(1, 1-dimethylethyl)cyclohexyl]amino]methyl]-2,3-dihydro-, trans- (9C1), Jun. 1, 1990, 1 page.

CAS Registry No. 127456-45-5, Phenol, 4-(1, 1-dimethylethyl)-2-[[[4-(1, 1-dimethylethyl)cyclohexyl]amino]methyl]-, trans- (9C1), Jun. 1, 1990, 1 page.

CAS Registry No. 127456-46-6, Phenol, 4-(1, 1-dimethylethyl)-2-[[[4-(1,1-dimethylethyl)cyclohexyl]amino]methyl]-6-methyl-, hydrochloride, trans-(9C1), Jun. 1, 1990, 1 page.

CAS Registry No. 127456-52-4, Phenol, 2-[[[4-(1, 1-dimethylethyl)cyclohexyl]amino]methyl]-4-(1-methylethyl)-, cis- (9C1), Jun. 1, 1990, 1 page.

CAS Registry No. 127456-56-8, Phenol, 4-chloro-2-[[[4-(1, 1-dimethylethyl)cyclohexyl]amino]methyl]-, trans- (9C1), Jun. 1, 1990, 1 page.

CAS Registry No. 127456-57-9, Phenol, 2-[[[4-(1, 1-dimethylethyl)cyclohexyl]amino]methyl]-4-fluoro-, trans- (9C1), Jun. 1, 1990, 1 page.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1, 1-dimethylpropyl)cyclohexyl]-2,3-difluoro-, Dec. 5, 2012, 1 page.

CAS Registry No. 1456349-79-3, Benzenemethanamine, 2,3-dichloro-N-[4-(1, 1-dimethylpropyl)cyclohexyl]-, Oct. 6, 2013, 1 page.

CAS Registry No. 1458497-71-6, Benzenemethanamine, 2,4-dichloro-N-[4-(1, 1-dimethylethyl)cyclohexyg-a-methyl-, Oct. 15, 2013, 1 page.

CAS Registry No. 1459328-13-2, Phenol, 2-bromo-4-[[[4-(1,1-dimethylpropyl)cyclohexyl]amino]methyl]-, Oct. 16, 2013, 1 page.

CAS Registry No. 1490220-45-5, Benzenemethanamine, 2-bromo-5-chloro-N-[4-(1,1-dimethylpropyl)cyclohexyl]-, Dec. 8, 2013, 1 page.

CAS Registry No. 1515984-46-9, Benzamide, N-(4-aminocyclohexyl)-3-chloro-N,5-dimethyl-, Jan. 10, 2014, 1 page.

CAS Registry No. 1542027-51-9, Phenol, 3-chloro-2-[[[4-(1,1-dimethylpropyl)cyclohexyl]amino]methyl]-, Feb. 11, 2014, 1 page.

CAS Registry No. 1624268-56-9, Benzamide, 4-[[[4-(1, 1-dimethylethyl)cyclohexyl]amino]methyl]-N-methyl-, Sep. 22, 2014, 1 page.

CAS Registry No. 1712122-27-4, Benzenemethanamine, 5-chloro-N-[4-(1,1-dimethylpropyl)cyclohexyl]-2-fluoro-, May 25, 2015, 1 page.

CAS Registry No. 1772618-27-5, Phenol, 3-[[[4-(1, 1-dimethylpropyl)cyclohexyl]amino]methyl]-5-fluoro-, Jun. 3, 2015, 1 page.

CAS Registry No. 1775706-37-0, Phenol, 2-chloro-6-[[[4-(1,1-dimethylpropyl)cyclohexyl]amino]methyl]-, Jun. 8, 2015, 1 page.

CAS Registry No. 1858436-76-6, Bicyclo[3.1.0]hexan-2-amine, N-[(3-chloro-5-methylphenyl)methyl]-, Feb. 3, 2016, 1 page.

CAS Registry No. 1931388-10-1, Benzenemethanamine, 2,5-dichloro-N-[4-(1,1-dimethylpropyl)cyclohexyl]-, Jun. 14, 2016, 1 page.

CAS Registry No. 1939264-55-7, Phenol, 4-[[[4-(1, 1-dimethylpropyl)cyclohexyl]amino]methyl]-2-fluoro-, Jun. 26, 2016, 1 page.

CAS Registry No. 1939792-99-0, Benzenemethanamine, 5-bromo-2-chloro-N-[4-(1, 1-dimethylpropyl)cyclohexyl]-, Jun. 27, 2016, 1 page.

CAS Registry No. 1962333-15-8, Benzenemethanamine, N-[4-(1, 1-dimethylpropyl)cyclohexyl]-5-fluoro-2-methyl-, Jul. 29, 2016, 1 page.

CAS Registry No. 2032268-58-7, Cyclohexanecarboxylic acid, 4-[[(3-chloro-5-methylphenyl)methyl]amino]-, Nov. 15, 2016, 1 page.

CAS Registry No. 2199998-08-6, Cyclohexanecarboxylic acid, 2-[[(3-chloro-5-methylphenyl)methyl]amino]-1-methyl-, Mar. 27, 2018, 1 page.

CAS Registry No. 2202151-69-5, Cyclohexanecarboxylic acid, 3-[[(3-chloro-5-methylphenyl)methyl]amino]-, Mar. 30, 2018, 1 page.

CAS Registry No. 2322790-81-6, Benzenemethanamine, N-[4-(1, 1-dimethylethyl)cyclohexyl]-3-(trifluoromethyl)-, Jun. 2, 2019, 1 page.

CAS Registry No. 2419600-39-6, Benzenemethanamine, 3-chloro-N-[4-(1,1-dimethylpropyl)cyclohexyl]-5-methyl-, Jun. 5, 2020, 1 page.

CAS Registry No. 415970-94-4, Benzenemethanamine, N-[4-(1, 1-dimethylethyl)cyclohexyl]-3,5-dimethoxy-, May 15, 2002, 1 page.

CAS Registry No. 744981-83-7, Phenol, 2,6-dibromo-4-[[[4-(1, 1-dimethylethyl)cyclohexyl]amino]methyl]-, Sep. 15, 2004, 1 page.

(56) References Cited

OTHER PUBLICATIONS

CAS Registry No. 793633-39-3, Phenol, 4-(1, 1-dimethylethyl)-2-[[[trans-4-(1,1-dimethylethyl)cyclohexyl]amino]methyl]-6-methyl-, Dec. 6, 2004, 1 page.

Chen et al., "Structure-activity relationships in a series of 5-[(2,5-dihydroxybenzyl)amino]salicylate inhibitors of EGF-receptor-associated tyrosine kinase: importance of additional hydrophobic aromatic interactions", Journal of Medicinal Chemistry, Mar. 18, 1994, pp. 845-859.

Cocchi et al., "Novel Psychoactive Phenethylamines: Impact on Genetic Material," International Journal of Molecular Sciences (2020), 21(24), 9616.

Demarinis et al., "alpha.-Adrenergic agents. 2. Synthesis and. alpha.1-agonist activity of 2-aminotetralins", Journal of Medicinal Chemistry, Feb. 1982, pp. 136-141.

Glennon et al., "Influence of Amine Substituents on 5-HT2A versus 5-HT2C Binding of Phenylalkyl- and Indolylalkylamines," Journal of Medicinal Chemistry (1994), 37(13), 1929-1935.

Gonzalez-Maeso et al., "Hallucinogens recruit specific cortical 5-HT2A receptor-mediated signaling pathways to affect behavior", Neuron, Feb. 2007, pp. 439-452.

Halberstadt, "Recent advances in the neuropsychopharmacology of serotonergic Hallucinogens", Behavioural Brain Research, Jan. 2015, pp. 99-120.

Hamada et al., "Water-soluble prodrugs of dipeptide HIV protease inhibitors based on O→N intramolecular acyl migration: Design, synthesis and kinetic study," Bioorg Med Chem., Jan. 2, 2004; 12(1):159-70.

Hansen et al., "Synthesis and pharmacological evaluation of N-benzyl substituted 4-bromo-2,5-dimethoxyphenethylamines as 5-HT2A/2C partial agonists," Bioorganic &Medicinal Chemistry (2015), 23(14), 3933-3937.

Hansen et al., "Synthesis and Structure-Activity Relationships of N-Benzyl Phenethylamines as 5-HT2A/2C Agonists," ACS Chemical Neuroscience (2014), 5(3), 243-249.

International Search Report and Written Opinion for International Application No. PCT/US2022/032918, mailed Oct. 12, 2022, 10 pages.

Invitation to Pay Fee for International Application No. PCT/US2022/082403 dated Mar. 8, 2023, 3 pages.

Kaminska et al., "25C-NBOMe short characterisation," Forensic Toxicology (2020) 38:490-495.

Kraehenmann et al., "Dreamlike effects of LSD on waking imagery in humans depend on serotonin 2A receptor activation", Psychopharmacology, Jul. 2017, pp. 2031-2046.

Kraehenmann et al., "LSD Increases Primary Process Thinking via Serotonin 2A Receptor Activation," Front. Pharmacol. (2017) 8:814, 9 pages.

Kucklander et al., "Darstellung and Oxidation von 2-(2,5-Dihydroxyphenyl)-ethylamin-Derivaten, II," Zeitschrift fuer Naturforschung, B: Chemical Sciences (1987), 42(12), 1567-77 (with English abstract).

Li et al., "Treatment of Breast and Lung Cancer Cells with a N-7 Benzyl Guanosine Monophosphate Tryptamine Phosphoramidate Pronucleotide (4Ei-1) Results in Chemosensitization to Gemcitabine and Induced eIF4E Proteasomal Degradation," Mol Pharm. Feb. 4, 2013; 10(2): 523-531, 19 pages.

Madsen et al., "Psychedelic effects of psilocybin correlate with serotonin 2A receptor occupancy and plasma psilocin levels", Neuropsychopharmacology, Jun. 2019, pp. 1328-1334.

Milne et al., "Metabolic engineering of *Saccharomyces cerevisiae* for the de novo production of psilocybin and related tryptamine derivatives," Metabolic Engineering, 60 (2020) 25-36.

Nichols et al., "Nonneurotoxic tetralin and indan analogs of 3,4-(methylenedioxy) amphetamine (MDA)", Journal of Medicinal Chemistry, Feb. 1990, pp. 703-710.

Nichols et al., "Potential psychotomimetics. 2. Rigid analogs of 2,5-dimethoxy-4-methylphenylisopropylamine (DOM, STP)", Journal of Medicinal Chemistry, Feb. 1974, pp. 161-166.

Nichols et al., "Structure-activity relationships of Phyenethylamine hallucinogens", Journal of Pharmaceutical Sciences, Aug. 1981, pp. 839-849.

Nichols, "Hallucinogens," Pharmacol. Ther. (2004) 101, 131-181.

Perez Custodio et al., "25B-NBOMe, a novel N-2-methoxybenzyl-phenethylamine (NBOMe) derivative, may induce rewarding and reinforcing effects via a dopaminergic mechanism: Evidence of abuse potential," Addiction Biology 2019;e12850, 12 pages.

Pokorny et al., "Modulatory effect of the 5-HT1A agonist buspirone and the mixed non-hallucinogenic 5-HT1A/2A agonist ergotamine on psilocybin-induced psychedelic experience," Eur. Neuropsychopharmacol. (2016) 26, 756-766.

Pottie et al., "Identification of psychedelic new psychoactive substances (NPS) showing biased agonism at the 5-HT2AR through simultaneous use of β-arrestin 2 and miniGaq bioassays," Biochemical Pharmacology, 2020, 182, 114251 (Peer reviewed author version, 38 pages).

Preller et al., "Effects of serotonin 2A/1A receptor stimulation on social exclusion processing," PNAS, May 3, 2016, vol. 113, No. 18, 5119-5124.

Preller et al., "Role of the 5-HT2A Receptor in Self- and Other-Initiated Social Interaction in Lysergic Acid Diethylamide-Induced States: A Pharmacological fMRI Study," J. Neurosci., Apr. 2018, 38(14): 3603-3611.

Preller et al., "The Fabric of Meaning and Subjective Effects in LSD-Induced States Depend on Serotonin 2A Receptor Activation," Current Biology, Feb. 2017, 27, 451-457.

Pubchem, SID 103414083, Modify Date: Feb. 17, 2021, 7 pages.

Pubchem, SID 103936367, Available Date: Mar. 28, 2023 [retrieved on Mar. 28, 2023]., Retrieved from the Internet [URL: https://pubchem.ncbi.nlm.nih. gov/substance/103936367], 6 pages.

PubChem SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.

PubChem-SID-310331158, Modify Date: Feb. 15, 2015, p. 2.

PubChem-SID-369863280, Modify Date: May 25, 2018, p. 2.

Sargent et al., "Radiohalogen-Labeled Imaging Agents. 3. Compounds for Measurement of Brain Blood Flow by Emission Tomography," Journal of Medicinal Chemistry (1984), 27(8), 1071-1077.

Schifano et al., "New psychoactive substances (NPS) and serotonin syndrome onset: A systematic review," Experimental Neurology (2021), 339, 113638 (Author manuscript, 29 pages).

Tirapegui et al., "Synthesis of N-(halogenated) benzyl analogs of superpotent serotonin ligands," J. Chil. Chem. Soc., (2014) 59, No. 3, pp. 2625-2627.

Titeler et al., "Radioligand binding evidence implicates the brain 5-HT2 receptor as a site of action for LSD and phenylisopropylamine hallucinogens," Psychopharmacology (1988) 94, 213-216.

International Search Report and Written Opinion for International Application No. PCT/US2022/032715 dated Nov. 17, 2022, 18 pages.

International Search Report and Written Opinion for PCT/US2022/082403, May 17, 2023, 15 pages.

Valle et al., "Inhibition of alpha oscillations through serotonin-2A receptor activation underlies the visual effects of ayahuasca in humans," Eur. Neuropsychopharm (2016) 26, 1161-1175 (Author-edited version, 23 pages).

Vollenweider et al., "Psilocybin induces schizophrenia-like psychosis in humans via a serotonin-2 agonist action," Neuroreport (1998) 9, 3897-3902 (8 pages).

Vollenweider et al., "Psychedelic drugs: neurobiology and potential for treatment of psychiatric disorders," Nature Reviews Neuroscience, Nov. 2020, vol. 21, pp. 611-624.

Winter et al., Psilocybin-induced stimulus control in the rat Pharmacol. Biochem. Behav. (2007) 87, 472-480 (18 pages).

Wood et al., "Prevalence of use and acute toxicity associated with the use of NBOMe drugs," Clinical Toxicology, 2015, 53:85-92.

Invitation to Pay Fee for International Application No. PCT/US2022/032715 dated Aug. 30, 2022, 2 pages.

Poulie et al., "Discovery of β-Arrestin-Biased 25CN-NBOH-Derived 5-HT2A Receptor Agonists." J Med Chem. Sep. 22, 2022; 65(18): 12031-12043. doi:10.1021/acs.jmedchem.2c00702. Epub Sep. 13, 2022.

(56) References Cited

OTHER PUBLICATIONS

Berge et al., "Pharmaceutical Salts," J Pharm. Sci., 1977; 66: 1-19.
Brandt et al., "Analytical characterization of bioactive N-benzyl-substituted phenethylamines and 5-methoxytryptamines"Rapid Commun., Mass Spectrum, 2015, 29, pp. 573-584.
International Search Report and Written Opinion for International Application No. PCT/US2023/085505, mailed Apr. 8, 2024, 11 pages.
International Search Report and Written Opinion for International Application No. PCT/US2023/085521, mailed Apr. 8, 2024, 13 pages.
International Search Report and Written Opinion for International Application No. PCT/US2024/019770, mailed Aug. 12, 2024. 22 pages.
International Search Report and Written Opinion for International Application No. PCT/US23/82981, mailed Apr. 4, 2024, 24 pages.
International Search Report and Written Opinion for PCT Application No. PCT/US2024/027296 mailed Aug. 13, 2024, 18 pages.
Kehne et al., "Preclinical characterization of the potential of the putative atypical antipsychotic MDL 100,907 as a potent 5-HT2A antagonist with a favorable CNS safety profile." J Pharmacol Exp Ther. May 1996; 277(2): 968-81.
Kennett et al. "SB 242084, a selective and brain penetrant 5-HT2C receptor antagonist", Neuropharmacology, (1997); 36(4-5): 609-620.
Klein et al., "Investigation of the Structure-Activity Relationships of Psilocybin Analogues." ACS Pharmacol. Transl. Sci. 2021, 4, 533-542.
National Center for Biotechnology Information "2-(2,5-Dimethoxy-4-methylsulfanyl-phenyl)-N-[(2-methoxyphenyl)methyl]ethanamine: Pubchem CID 124518722" Pubchem entry (online), Apr. 10, 2017; Retrieved on Feb. 17, 2024 from the Internet: [URL:https://pubchem.ncbi.nlm.nih.gov/compound/124518722]; 13 pages.
National Center for Biotechnology Information 2-[2,5-dimethoxy-4-(methylsulfonimidoyl)phenyl]-N-[(3-fluoro-5-methylphenyl)methyl]ethanamine: Pubchem CID 167226743 Pubchem entry (online), pp. 1-9, Mar. 21, 2023, URL:https://pubchem.nlm.nih.gov/compound/167226743.
National Center for Biotechnology Information, "2-(2,5-dimethoxyphenyl)-N-(pyridin-2-ylmethyl)ethanamine: Pubchem CID 39371636" Pubchem entry (online), created May 29, 2009, Modified Oct. 12, 2024, [URL: https://pubchem.ncbi.nlm.nih.gov/compound/39371636]; 7 pages.
National Center for Biotechnology Information "N-[(3-chloro-5-methylphenyl)methyl]-2-[2,5-dimethoxy-4-(methylsulfonimidoyl)phenyl]ethanamine Pubchem CID 167226858" Pubchem entry (online), pp. 1-8, Mar. 21, 2023, URL: https://pubchem.ncbi.nim.nih.gov/compound/167226858.
National Center for Biotechnology Information "N-benzyl-2,5-dimethoxy-phenethylamine: Pubchem CID 13836160" PubChem entry (online), pp. 1-9, Feb. 8, 2007; URL: https://pubchem.ncbi.nlm.nih.gov/compound/13836160. 9 pages.
Pubchem SID 387777206, Modify Date: Dec. 6, 2019 Retrieved from the Internet URL: https://pubchem.ncbi.nlm.nih.gov/substance/387777206, 5 pages.
Pubchem, SID 472180752, Modify Date: Oct. 11, 2022 [retrieved on Feb. 21, 2024]. Retrieved from the Internet URL: https://pubchem.ncbi.nlm.nih.gov/substance/472180752, 5 pages.
Tomaszewski et al., "Benzofuran Bioisosteres of Hallucinogenic Tryptamines," J. Med. Chem., 1992, 35, pp. 2061-2064.
U.S. Appl. No. 18/532,940, filed Dec. 7, 2023, by Khan et al.

* cited by examiner

AMINOTETRALINE ACTIVATORS OF SEROTONIN RECEPTORS

CROSS-REFERENCE TO RELATED APPLICATION

The present application is a continuation of U.S. application Ser. No. 18/146,785, filed on Dec. 27, 2022, now U.S. Pat. No. 11,827,580, issued Nov. 28, 2023, which claims the benefit of priority to U.S. Provisional Application No. 63/294,030, filed Dec. 27, 2021, the contents of which both are hereby incorporated by reference in its entirety.

BACKGROUND

Psychedelics can be classified into three main classes: indoleamines, phenylalkylamines, and ergolines. The first class, indolamines include N,N-dimethyltryptamine (DMT), 5-methoxy-DMT (5-MeO-DMT), psilocybin and 4-hydroxy-DMT. The second class, phenylalkylamines, include mescaline, as well as synthetic mescaline analogs such as 2,5-dimethoxy-4-iodoamphetamine (DOI) and 2,5-dimethoxy-4-bromoamphetamine (DOB). The third class are ergolines, such as LSD. The phenylalkylamines are selective agonists of 5-HT2 receptors, including 5-HT2A, 5-HT2B and 5-HT2C receptors. The indoleamines and ergolines act as partial agonists of 5-HT1, 5-HT2, 5-HT6 and 5-HT7 receptors. LSD and other ergolines also act upon D1 and D2 dopamine receptors and adrenergic receptors.

Activation of 5-HT2A receptors located in cortical and subcortical structures of the brain are thought to mediate the subjective, behavioral, and psychological effects of psychedelics in both animals and humans. Serotonergic psychedelics have demonstrated potential for treating a range of mental health diseases or disorders.

There remains a need for compounds that act as agonists of serotonin receptors, such as the 5-HT2A receptor as well as compositions and methods of use thereof.

SUMMARY

In one aspect, the present disclosure provides compounds which act as agonists of serotonin receptors e.g., the 5-HT2A receptor, as well as compositions and methods of use thereof e.g., for the treatment of a mental health disease or disorder.

In embodiments, the present disclosure provides a compound of Formula (I):

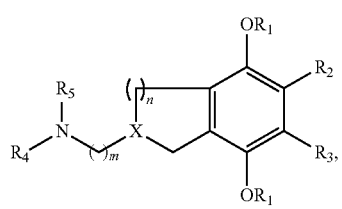

or a pharmaceutically acceptable salt thereof; wherein,
$R_1$ is independently H, $C_1$-$C_6$ alkyl, $C_1$-$C_6$ fluoroalkyl;
$R_2$ and $R_3$ are independently H, $C_1$-$C_6$ alkyl, $C_1$-$C_6$ fluoroalkyl, halogen, CN, $OR_1$ S(O)NHR$IR_2$, or $SR_1$;
$R_4$ and $R_5$ are independently H, $C_1$-$C_6$ alkyl, $C_1$-$C_6$ fluoroalkyl;
X is C or N;
m is 0, 1, 2 or 3; and
n is 0, 1, 2 or 3;
wherein the compound is not 5,8-dimethoxy-1,2,3,4-tetrahydronaphthalen-2-amine; 5,8-dimethoxy-N-methyl-1,2,3,4-tetrahydronaphthalen-2-amine; or (5,8-dimethoxy-1,2,3,4-tetrahydronaphthalen-2-yl)methanamine.

In embodiments, the compound of Formula (I) is a compound of Formula (I-A):

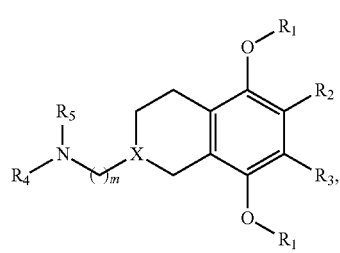

wherein $R_1$, $R_2$, $R_3$ $R_4$, $R_5$, X and m have the definitions provided herein.

In embodiments, the present disclosure provides a compound of Formula (II):

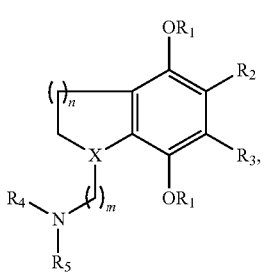

or a pharmaceutically acceptable salt thereof; wherein,
$R_1$ is independently H, $C_1$-$C_6$ alkyl, $C_1$-$C_6$ fluoroalkyl;
$R_2$ and $R_3$ are independently H, $C_1$-$C_6$ alkyl, $C_1$-$C_6$ fluoroalkyl, halogen, CN, $OR_1$ S(O)NHR$IR_2$, or $SR_1$;
$R_4$ and R 5 are independently H, $C_1$-$C_6$ alkyl, $C_1$-$C_6$ fluoroalkyl;
X is C or N;
m is 0, 1, 2 or 3; and
n is 0, 1, 2 or 3;
wherein the compound is not (5,8-dimethoxy-1,2,3,4-tetrahydronaphthalen-1-yl)methanamine.

In embodiments, the compound of Formula (II) is a compound of Formula (II-A):

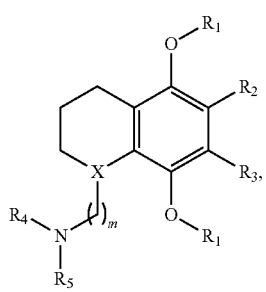

wherein $R_1$, $R_2$, $R_3$, $R_4$, $R_5$, X and m have the definitions provided herein.

In embodiments, the present disclosure provides a compound of Formula (III):

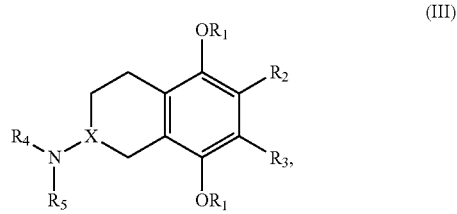

(III)

or a pharmaceutically acceptable salt thereof; wherein,
$R_1$ is independently methyl or $C_2$-$C_6$ fluoroalkyl;
$R_2$ and $R_3$ are independently H, $C_1$-$C_6$ alkyl, $C_1$-$C_6$ fluoroalkyl, halogen, CN, $OR_7$ or —S(O)(Y)$R_6$;
Y is =O or =NH;
$R_4$ and R 5 are independently H or $C_1$-$C_6$ fluoroalkyl;
$R_6$ and $R_7$ are independently H, $C_1$-$C_6$ alkyl, or $C_1$-$C_6$ fluoroalkyl; and
X is CH or N;
wherein the compound is not 5,8-dimethoxy-6-methyl-1,2,3,4-tetrahydronaphthalen-2-amine; 5,8-dimethoxy-1,2,3,4-tetrahydronaphthalen-2-amine; 6-bromo-5,8-dimethoxy-1,2,3,4-tetrahydronaphthalen-2-amine; 7-bromo-5,8-dimethoxy-1,2,3,4-tetrahydronaphthalen-2-amine; 5,7,8-trimethoxy-1,2,3,4-tetrahydronaphthalen-2-amine; or 5,6,8-trimethoxy-1,2,3,4-tetrahydronaphthalen-2-amine.

In embodiments, the present disclosure provides a compound of Formula (III-A):

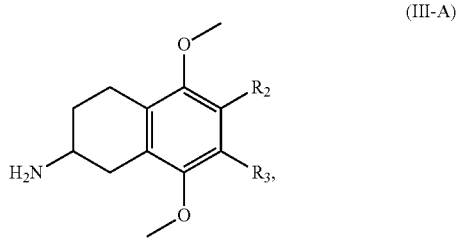

(III-A)

wherein $R_2$ and $R_3$ have definitions as provided herein.

In embodiments, the present disclosure provides a compound of Formula (IV):

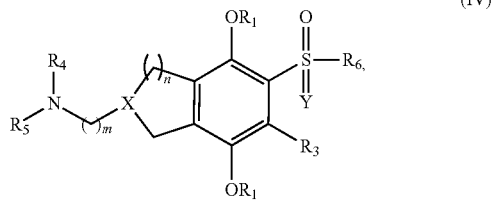

(IV)

or a pharmaceutically acceptable salt thereof; wherein,
$R_1$ is independently H, $C_1$-$C_6$ alkyl, or $C_1$-$C_6$ fluoroalkyl;
$R_3$ is H, $C_1$-$C_6$ alkyl, $C_1$-$C_6$ fluoroalkyl, halogen, CN, $OR_7$ or $SR_1$;

$R_4$ and R 5 are independently H, $C_1$-$C_6$ alkyl, or $C_1$-$C_6$ fluoroalkyl;
$R_6$ and $R_7$ are independently H, $C_1$-$C_6$ alkyl, or $C_1$-$C_6$ fluoroalkyl;
X is CH or N;
m is 0, 1, 2 or 3; and
n is 0, 1, 2 or 3. In embodiments, the present disclosure provides a compound of Formula (IV-A):

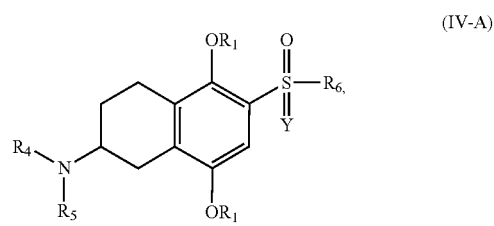

(IV-A)

wherein $R_1$, $R_4$, $R_5$, $R_6$, and Y have the definitions provided herein.

DETAILED DESCRIPTION

Figure 1A:
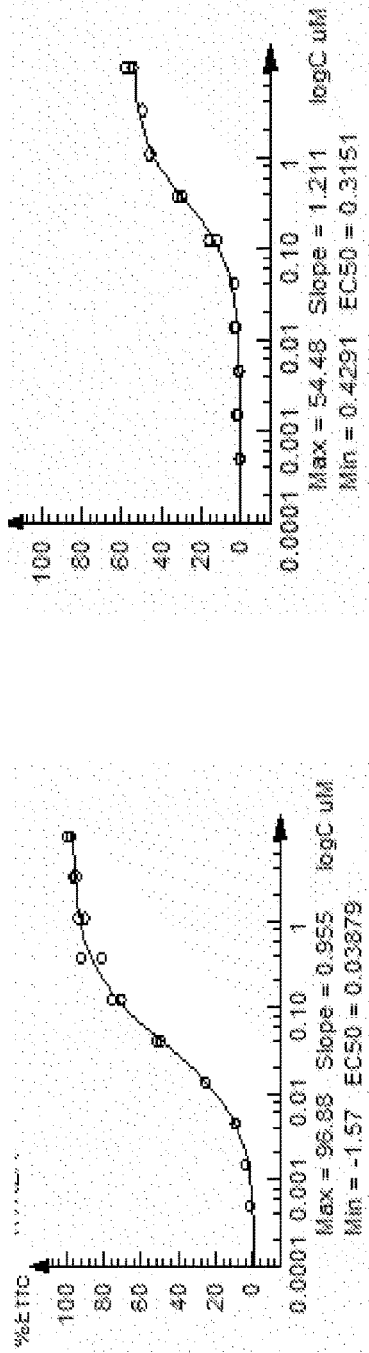
FIG. 1A shows EC50 profiles of Compounds 1-2 and 1-1, comparing 5-HT2A and 5-HT2B activity.
Figure 1A:
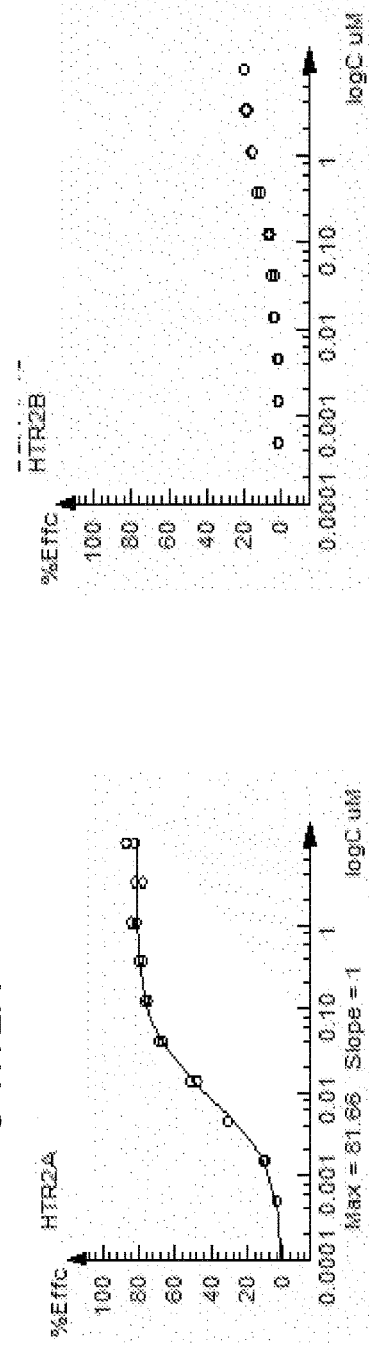
Figure 1A:
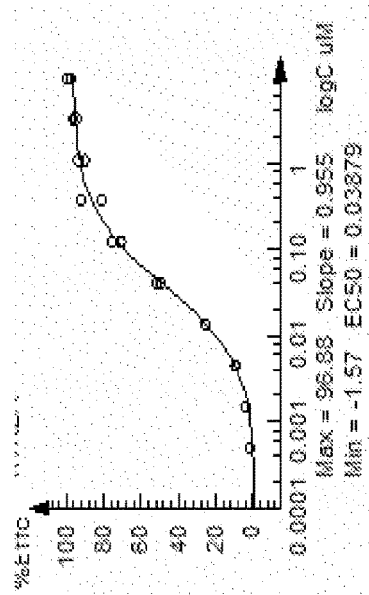
Figure 1A:
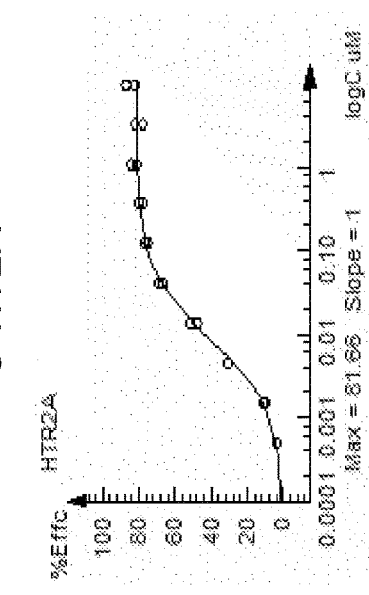

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to administering a compound or pharmaceutically acceptable salt of the compound or a composition or formulation comprising the compound or pharmaceutically acceptable salt of the compound to a patient.

The term "treating" as used herein with regard to a patient or subject, refers to improving at least one symptom of the patient's or subject's disorder. In embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes Cn and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkoxy" refers to a group of the formula -$OR_a$ where $R_a$ is an alkyl, alkenyl or alknyl as defined above containing one to twelve carbon atoms. Unless stated otherwise specifically in the specification, an alkoxy group can be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

The term "substituted" used herein means any of the groups described herein (e.g., alkyl, alkenyl, alkynyl, alkoxy, aryl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Compounds

In one aspect, the present disclosure provides compounds that are agonists of the 5-HT2A receptor. In embodiments, the compounds are full agonists of the 5-HT2A receptor. In embodiments, the compounds are partial agonists of the 5-HT2A receptor. In embodiments, the compounds selectively bind to the 5-HT2A receptor. In embodiments, the compounds of the present disclosure are compounds of Formula (I), (I-A), (I-B), (II), (II-A), (II-B), (III), (III-A), (IV) and (IV-A).

Activation of 5-HT2A receptors located in cortical and subcortical structures of the brain are thought to mediate the subjective, behavioral and psychological effects of psychedelics in both animals and humans. In rodents, psychedelics have been shown to elicit a 'head twitch response' which has been demonstrated to be a direct and selective consequence of 5-HT2A activation over other similar serotonin receptors including both 5-HT2C and 5-HT2B (Halberstadt, A. L., Behav. Brain Res. 277, 99-120 (2015); Winter et al., Pharmacol. Biochem. Behav. 87, 472-480 (2007); Benneyworth et al., Psychopharmacology 179, 854-862 (2005); Titeler et al, Psychopharmacology, 94, 213-216 (1988)). Similar observations have been made in humans where the administration of ketanserin, a 5-HT2A receptor antagonist, blocked the majority of subjective effects induced by DMT, psilocyin and LSD (Preller, Curr. Biol. 27, 451-457 (2017); Preller, J. Neurosci. 38, 3603-3611 (2018); Kraehenmann, Front. Pharmacol. 8, 814 (2017); Kraehenmann, Psychopharmacology 234, 2031-2046 (2017); Vollenweider, Neuroreport 9, 3897-3902 (1998); Preller, Acad. Sci. USA11 3, 5119-5124 (2016); Valle, Eur. Neuropsychopharm 26, 1161-1175 (2016)). In addition, psychedelic effects elicited by psilocybin have correlated with 5-HT2A receptor occupancy as measured by positron emission tomography in the prefrontal cortex (PFC) and other cortical regions in humans (Madsen, Neuropsychopharmacology 44, 1328-1334 (2019)). While 5-HT2A is the predominant driver of psychedelic effects in humans, other serotonin receptors, like 5-HT1A, are likely contributing to the overall psychedelic experience including both visual and attention-disrupting effects in humans (Pokorny et al., Eur. Neuropsychopharmacol. 26, 756-766 (2016); Carter et al., Neuropsychopharmacology 30, 1154-1162 (2005)).

Biased signaling consequences of 5-HT2A activation by various agonists strongly impact whether or not a compound will be hallucinogenic or non-hallucinogenic. For example, LSD and lisuride both activate the 5-HT2A receptor but in slightly different ways which result in the activation of different intracellular signaling cascades. LSD and lisuride have been shown to activate canonical Gq-based signaling downstream of 5-HT2A, but only LSD stimulated the expression of early growth response proteins (EGR1 and EGR2) by activating Gi/o subunits and the SRC protein kinase (Gonzalez-Maeso et al, Neuron 53, 439-452 (2007)). Differential functional selectivity has been shown for several phenalkylamine pyschedelics which were found to be biased 5-HT2A agonists (Pottie et al, Biochemical pharmacology, 182, 114251, 2020). The compounds, including 25H-NBF, 25H-NBMD, 25H-NBOH and 25H-NBOMe showed a statistically significant preference towards the recruitment of β-arrestin 2 over miniGaq, as compared to the reference psychedelic substance LSD.

Differential biased agonism elicited across multiple classes of psychedelics warrants further investigation to identify whether this functional selectivity may provide compounds with greater selectivity, fewer side effects, greater neuroplastic effects and improved therapeutic benefit.

Studies of aminotetralines such as lysergic acid congeners demonstrated that while 2-amino-5,8-dimethoxy-6-methyl-1,2,3,4-terahydronaphthalene has activity at 5-HT receptors, the compound failed to elicit common psychedelic side effects in rats in comparison to mescaline or 2,5-dimethoxy-4-methylphenylisopropylamine at similar doses (Nichols et al, 1974). Additional drug discrimination studies in LSD-trained rats and MDMA-trained rats found that stimulus generalization did not occur with any of the 2-aminotetralins studied suggesting that consistent with previous studies the tetralin congeners are most likely not hallucinogenic (Nichols et al, 1990).

Formula (I):

In embodiments, the present disclosure provides a compound of Formula (I):

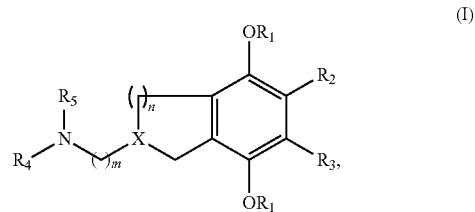

or a pharmaceutically acceptable salt thereof; wherein, $R_1$ is independently H, $C_1$-$C_6$ alkyl, or $C_1$-$C_6$ fluoroalkyl;

$R_2$ and $R_3$ are independently H, $C_1$-$C_6$ alkyl, $C_1$-$C_6$ fluoroalkyl, halogen, CN, $OR_1$, $S(O)NHRIR_2$, or $SR_1$;

$R_4$ and $R_5$ are independently H, $C_1$-$C_6$ alkyl, $C_1$-$C_6$ fluoroalkyl;

X is CH or N;

m is 0, 1, 2 or 3; and n is 0, 1, 2 or 3;

wherein the compound is not 5,8-dimethoxy-1,2,3,4-tetrahydronaphthalen-2-amine; 5,8-dimethoxy-N-methyl-1,2,3,4-tetrahydronaphthalen-2-amine; or (5,8-dimethoxy-1,2,3,4-tetrahydronaphthalen-2-yl) methanamine.

In embodiments, the present disclosure provides a compound of Formula (I-A):

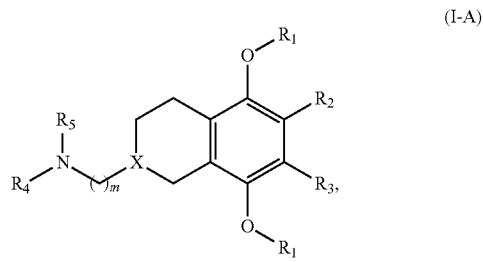

wherein $R_1$, $R_2$, $R_3$ $R_4$, $R_5$, X and m have the definitions provided herein.

In embodiments, the present disclosure provides a compound of Formula (I-B):

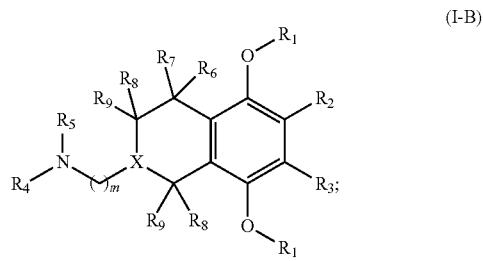

wherein,

R$_6$, R$_7$, R$_8$, and R$_9$ are independently H, C$_1$-C$_6$ alkyl, C$_1$-C$_6$ fluoroalkyl, halogen, CN, or R$_6$ and R$_7$ taken together with the atoms to which they are attached form a C$_3$-C$_7$ carbocycle, or R$_8$, and R$_9$, taken together with the atoms to which they are attached form a C$_3$-C$_7$ carbocycle; and wherein when X is N, R$_8$ and R$_9$ are not halogen or CN.

In embodiments of the compounds of Formula (I), (I-A) or (I-B), R$_1$ is independently C$_1$-C$_6$ alkyl.

In embodiments of the compounds of Formula (I), (I-A) or (I-B), R$_1$ is methyl.

In embodiments of the compounds of Formula (I), (I-A) or (I-B), R$_2$ and R$_3$ are independently H or C$_1$-C$_6$ alkyl.

In embodiments of the compounds of Formula (I), (I-A) or (I-B), R$_2$ and R$_3$ are independently H, methyl or ethyl.

In embodiments of the compounds of Formula (I), (I-A) or (I-B), R$_2$ and R$_3$ are independently H or C$_1$-C$_6$ fluoroalkyl.

In embodiments of the compounds of Formula (I), (I-A) or (I-B), R$_2$ and R$_3$ are independently H or trifluoromethyl.

In embodiments of the compounds of Formula (I), (I-A) or (I-B), R$_2$ and R$_3$ are independently H, F, Cl, Br, I or CN.

In embodiments of the compounds of Formula (I), (I-A) or (I-B), R$_2$ and R$_3$ are independently H or halogen.

In embodiments of the compounds of Formula (I), (I-A) or (I-B), R$_2$ and R$_3$ are independently H or I.

In embodiments of the compounds of Formula (I), (I-A) or (I-B), R$_2$ and R$_3$ are independently H or OR$_1$.

In embodiments of the compounds of Formula (I), (I-A) or (I-B), R$_2$ and R$_3$ are independently H or SR$_1$.

In embodiments of the compounds of Formula (I), (I-A) or (I-B), at least one of R$_2$ and R$_3$ is H.

In embodiments of the compounds of Formula (I), (I-A) or (I-B), R$_2$ and R$_3$ are independently H, C$_1$-C$_6$ alkyl, C$_1$-C$_6$ haloalkyl, halogen, cyano, OR$_1$ or SR$_1$, wherein at least one of R$_2$ and R$_3$ is H.

In embodiments of the compounds of Formula (I), (I-A) or (I-B), R$_2$ and R$_3$ are independently H, C$_1$-C$_6$ alkyl, halogen, cyano, OR1 or SR$_1$, wherein at least one of R$_2$ and R$_3$ is H.

In embodiments of the compounds of Formula (I), (I-A) or (I-B), R$_2$ and R$_3$ are independently H, halogen. C$_1$-C$_6$ alkyl, or C$_1$-C$_6$ haloalkyl, wherein at least one of R$_2$ and R$_3$ is H.

In embodiments of the compounds of Formula (I), (I-A) or (I-B), R$_2$ and R$_3$ are independently H, halogen, C$_1$-C$_3$ alkyl, or C$_1$-C$_3$ haloalkyl, wherein at least one of R$_2$ and R$_3$ is H.

In embodiments of the compounds of Formula (I), (I-A) or (I-B), R$_2$ and R$_3$ are independently H, C$_1$-C$_6$ alkyl, or C$_1$-C$_6$ haloalkyl, wherein at least one of R$_2$ and R$_3$ is H.

In embodiments of the compounds of Formula (I), (I-A) or (I-B), R$_2$ and R$_3$ are independently H, C$_1$-C$_3$ alkyl, or C$_1$-C$_6$ haloalkyl, wherein at least one of R$_2$ and R$_3$ is H.

In embodiments of the compounds of Formula (I), (I-A) or (I-B), R$_2$ and R$_3$ are independently H, or C$_1$-C$_6$ alkyl, wherein at least one of R$_2$ and R$_3$ is H.

In embodiments of the compounds of Formula (I), (I-A) or (I-B), R$_2$ and R$_3$ are independently H, or C$_1$-C$_3$ alkyl, wherein at least one of R$_2$ and R$_3$ is H.

In embodiments of the compounds of Formula (I), (I-A) or (I-B), R$_2$ and R$_3$ are independently H, —CF$_3$, methyl or ethyl, wherein at least one of R$_2$ and R$_3$ is H.

In embodiments of the compounds of Formula (I), (I-A) or (I-B), R$_2$ and R$_3$ are independently H, methyl or ethyl, wherein at least one of R$_2$ and R$_3$ is H.

In embodiments of the compounds of Formula (I), (I-A) or (I-B), R$_2$ and R$_3$ are independently H or methyl, wherein at least one of R$_2$ and R$_3$ is H.

In embodiments of the compounds of Formula (I), (I-A) or (I-B), R$_4$ and R$_5$ are independently H, methyl, ethyl or propyl.

In embodiments of the compounds of Formula (I), (I-A) or (I-B), R$_4$ and R$_5$ are independently H or methyl.

In embodiments of the compounds of Formula (I), (I-A) or (I-B), R$_4$ and R$_5$ are independently H or methyl.

In embodiments of the compounds of Formula (I), (I-A) or (I-B), at least one of R$_4$ and R$_5$ is H.

In embodiments of the compounds of Formula (I), (I-A) or (I-B), R$_4$ is H.

In embodiments of the compounds of Formula (I), (I-A) or (I-B), R$_4$ is methyl.

In embodiments of the compounds of Formula (I), (I-A) or (I-B), R$_4$ is ethyl.

In embodiments of the compounds of Formula (I), (I-A) or (I-B), R$_5$ is H.

In embodiments of the compounds of Formula (I), (I-A) or (I-B), X is CH.

In embodiments of the compounds of Formula (I), (I-A) or (I-B), X is N.

In embodiments of the compounds of Formula (I), (I-A) or (I-B), m is 0.

In embodiments of the compounds of Formula (I), (I-A) or (I-B), m is 1.

In embodiments of the compounds of Formula (I), n is 2.

In embodiments, the present disclosure provides a compound selected from Table 1.

In embodiments, the present disclosure provides a compound selected from Table 1 or a pharmaceutically acceptable salt thereof.

TABLE 1

Compounds

| No. | Structure | 5HT2A activation (%) max @ 30 and 03 µM |
|---|---|---|
| 1-1 | 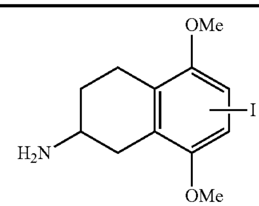 | 72.2/55.4 |
| 1-2 | 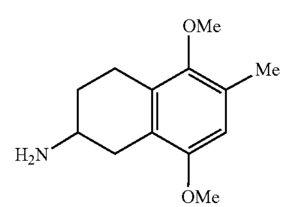 [SMILES: COc1cc(C)c(OC)c2c1CC(N)CC2] | 81.9/60.9 |
| 1-3 | 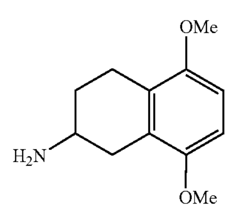 [SMILES: COc1ccc(OC)c2c1CCC(N)C2] | 67.1/12.1 |

TABLE 1-continued

Compounds

| No. | Structure | 5HT2A activation (%) max @ 30 and 03 μM |
|---|---|---|
| 1-4 | (tetralin with 5,8-diOMe and 2-NHMe) | 20.3/8.5 |
| 1-5 | (tetralin with 5,8-diOMe, 6-Br, 2-NH₂) | 82.7/73.8 |
| 1-6 | (tetralin with 5,8-diOMe, 6-Cl, 2-NH₂) | 66.6/64 |
| 1-7 | (tetralin with 5,8-diOMe, 6-CN, 2-NH₂) | — |
| 3-1 | (tetralin with 5,8-diOMe, 1-CH₂NH₂) | 53/1.5 |

In embodiments, the present disclosure provides a compound selected from Table 2 or a or a pharmaceutically acceptable salt thereof.

TABLE 2

Compounds

| No. | Structure |
|---|---|
| 2-1 | (tetralin with 5,8-diOMe, 6-I, 2-NH₂) |
| 2-2 | (tetralin with 5,8-diOMe, 7-I, 2-NH₂) |
| 2-3 | (tetrahydroisoquinoline with 5,8-diOMe, 2-NHEt) |
| 2-4 | (tetrahydroisoquinoline with 5,8-diOMe, 2-NHMe) |
| 2-5 | (tetralin with 5,8-diOMe, 2-CH₂NH₂) |
| 2-6 | (tetralin with 5,8-diOMe, 6-Me, 2-NH₂) |
| 2-7 | (tetralin with 5,8-diOMe, 6-SO₂Me, 2-NH₂) |

TABLE 2-continued

Compounds

| No. | Structure |
|---|---|
| 2-8 | 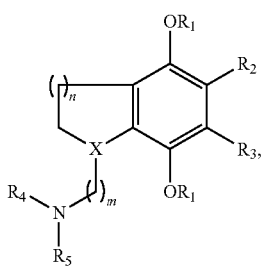 |
| 2-9 | 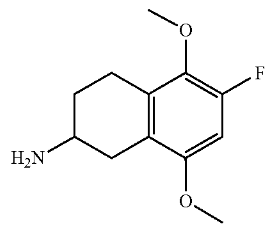 [SMILES: COc1cc(F)c(OC)c2c1CC(N)CC2] |
| 2-10 | 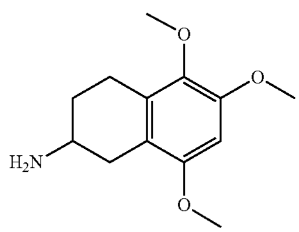 [SMILES: COc1cc(OC)c(OC)c2c1CC(N)CC2] |

Formula (II):

In embodiments, the present disclosure provides a compound of Formula (II):

(II)

or a pharmaceutically acceptable salt thereof; wherein, $R_1$ is independently H, $C_1$-$C_6$ alkyl, or $C_1$-$C_6$ fluoroalkyl;

$R_2$ and $R_3$ are independently H, $C_1$-$C_6$ alkyl, $C_1$-$C_6$ fluoroalkyl, halogen, CN, S(O)NHR$_1$R$_2$, OR$_1$ or SR$_1$;

$R_4$ and R 5 are independently H, $C_1$-$C_6$ alkyl, $C_1$-$C_6$ fluoroalkyl;

X is CH or N;

m is 0, 1, 2 or 3; and n is 0, 1, 2 or 3;

wherein the compound is not (5,8-dimethoxy-1,2,3,4-tetrahydronaphthalen-1-yl)methanamine.

In embodiments, the present disclosure provides a compound of Formula (II-A):

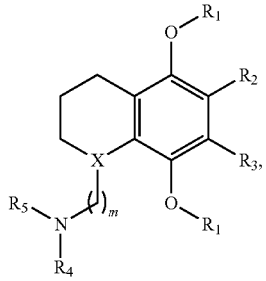

(II-A)

wherein $R_1$, $R_2$, $R_3$ $R_4$, $R_5$, X and m have the definitions provided herein.

In embodiments, the present disclosure provides a compound of Formula (II-B):

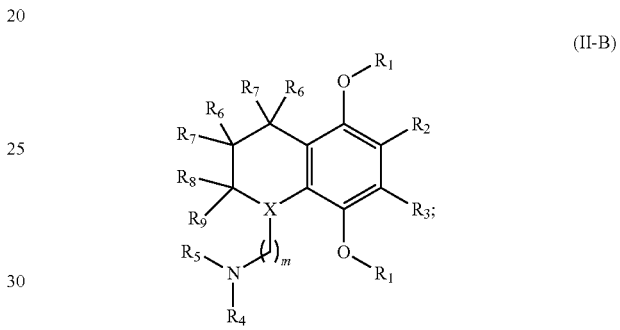

(II-B)

wherein, $R_6$, $R_7$, $R_8$, and $R_9$ are independently H, $C_1$-$C_6$ alkyl, $C_1$-$C_6$ fluoroalkyl, halogen, CN, or $R_6$ and $R_7$ taken together with the atoms to which they are attached form a $C_3$-$C_7$ carbocycle, or $R_8$, and $R_9$ taken together with the atoms to which they are attached form a $C_3$-$C_7$ carbocycle; and wherein X is N, $R_8$ and $R_9$ are not halogen or CN.

$R_2$ and $R_3$ are S(O)NHRIR$_2$.

In embodiments of the compounds of Formula (II), (II-A) or (II-B), $R_1$ is independently $C_1$-$C_6$ alkyl.

In embodiments of the compounds of Formula (II), (II-A) or (II-B), $R_1$ is methyl.

In embodiments of the compounds of Formula (II), (II-A) or (II-B), $R_2$ and $R_3$ are independently H or $C_1$-$C_6$ alkyl.

In embodiments of the compounds of Formula (II), (II-A) or (II-B), $R_2$ and $R_3$ are independently H, methyl or ethyl.

In embodiments of the compounds of Formula (II), (II-A) or (II-B), $R_2$ and $R_3$ are independently H or $C_1$-$C_6$ fluoroalkyl.

In embodiments of the compounds of Formula (II), (II-A) or (II-B), $R_2$ and $R_3$ are independently H or trifluoromethyl.

In embodiments of the compounds of Formula (II), (II-A) or (II-B), $R_2$ and $R_3$ are independently H, F, Cl, Br, I or CN.

In embodiments of the compounds of Formula (II), (II-A) or (II-B), $R_2$ and $R_3$ are independently H or halogen.

In embodiments of the compounds of Formula (II), (II-A) or (II-B), $R_2$ and $R_3$ are independently H or I.

In embodiments of the compounds of Formula (II), (II-A) or (II-B), $R_2$ and $R_3$ are independently H or OR$_1$.

In embodiments of the compounds of Formula (II), (II-A) or (II-B), $R_2$ and $R_3$ are independently H or SR$_1$.

In embodiments of the compounds of Formula (II), (II-A) or (II-B), at least one of $R_2$ and $R_3$ is H.

In embodiments of the compounds of Formula (II), (II-A) or (II-B), $R_2$ and $R_3$ are independently H, $C_1$-$C_6$ alkyl, $C_1$-$C_6$ haloalkyl, halogen, cyano, $OR_1$ or $SR_1$, wherein at least one of $R_2$ and $R_3$ is H.

In embodiments of the compounds of Formula (II), (II-A) or (II-B), $R_2$ and $R_3$ are independently H, $C_1$-$C_6$ alkyl, halogen, cyano, ORI or $SR_1$, wherein at least one of $R_2$ and $R_3$ is H.

In embodiments of the compounds of Formula (II), (II-A) or (II-B), $R_2$ and $R_3$ are independently H, halogen. $C_1$-$C_6$ alkyl, or $C_1$-$C_6$ haloalkyl, wherein at least one of $R_2$ and $R_3$ is H.

In embodiments of the compounds of Formula (II), (II-A) or (II-B), $R_2$ and $R_3$ are independently H, halogen, $C_1$-$C_3$ alkyl, or $C_1$-$C_3$ haloalkyl, wherein at least one of $R_2$ and $R_3$ is H.

In embodiments of the compounds of Formula (II), (II-A) or (II-B), $R_2$ and $R_3$ are independently H, $C_1$-$C_6$ alkyl, or $C_1$-$C_6$ haloalkyl, wherein at least one of $R_2$ and $R_3$ is H.

In embodiments of the compounds of Formula (II), (II-A) or (II-B), $R_2$ and $R_3$ are independently H, $C_1$-$C_3$ alkyl, or $C_1$-$C_5$ haloalkyl, wherein at least one of $R_2$ and $R_3$ is H.

In embodiments of the compounds of Formula (II), (II-A) or (II-B), $R_2$ and $R_3$ are independently H, or $C_1$-$C_6$ alkyl, wherein at least one of $R_2$ and $R_3$ is H.

In embodiments of the compounds of Formula (II), (II-A) or (II-B), $R_2$ and $R_3$ are independently H, or $C_1$-$C_3$ alkyl, wherein at least one of $R_2$ and $R_3$ is H.

In embodiments of the compounds of Formula (II), (II-A) or (II-B), $R_2$ and $R_3$ are independently H, —$CF_3$, methyl or ethyl, wherein at least one of $R_2$ and $R_3$ is H.

In embodiments of the compounds of Formula (II), (II-A) or (II-B), $R_2$ and $R_3$ are independently H, methyl or ethyl, wherein at least one of $R_2$ and $R_3$ is H.

In embodiments of the compounds of Formula (II), (II-A) or (II-B), $R_2$ and $R_3$ are independently H or methyl, wherein at least one of $R_2$ and $R_3$ is H.

In embodiments of the compounds of Formula (II), (II-A) or (II-B), $R_4$ and $R_5$ are independently H, methyl, ethyl or propyl.

In embodiments of the compounds of Formula (II), (II-A) or (II-B), $R_4$ and $R_5$ are independently H or methyl.

In embodiments of the compounds of Formula (II), (II-A) or (II-B), at least one of $R_4$ and $R_5$ is H.

In embodiments of the compounds of Formula (II), (II-A) or (II-B), $R_4$ is H.

In embodiments of the compounds of Formula (II), (II-A) or (II-B), $R_4$ is methyl.

In embodiments of the compounds of Formula (II), (II-A) or (II-B), $R_4$ is ethyl.

In embodiments of the compounds of Formula (II), (II-A) or (II-B), $R_5$ is H.

In embodiments of the compounds of Formula (II), (II-A) or (II-B), X is CH.

In embodiments of the compounds of Formula (II), (II-A) or (II-B), X is N.

In embodiments of the compounds of Formula (II), (II-A) or (II-B), m is 0.

In embodiments of the compounds of Formula (II), (II-A) or (II-B), m is 1.

In embodiments of the compounds of Formula (II), n is 2.

In embodiments, the present disclosure provides compound (3-1) or a pharmaceutically acceptable salt thereof:

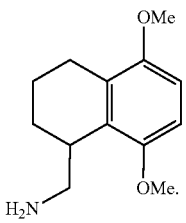

(3-1)

Formula (III):

In embodiments, the present disclosure provides a compound of Formula (III):

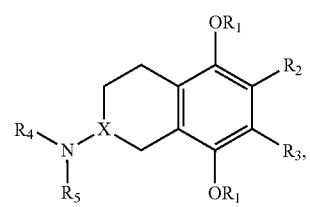

(III)

or a pharmaceutically acceptable salt thereof; wherein, $R_1$ is independently methyl or $C_2$-$C_6$ fluoroalkyl;

$R_2$ and $R_3$ are independently H, $C_1$-$C_6$ alkyl, $C_1$-$C_6$ fluoroalkyl, halogen, CN, $OR_7$ or —S(O)(Y)$R_6$;

Y is =O or =NH;

$R_4$ and R 5 are independently H or $C_1$-$C_6$ fluoroalkyl;

$R_6$ and $R_7$ are independently H, $C_1$-$C_6$ alkyl, or $C_1$-$C_6$ fluoroalkyl; and X is CH or N;

wherein the compound is not 5,8-dimethoxy-6-methyl-1,2,3,4-tetrahydronaphthalen-2-amine; 5,8-dimethoxy-1,2,3,4-tetrahydronaphthalen-2-amine; 6-bromo-5,8-dimethoxy-1,2,3,4-tetrahydronaphthalen-2-amine; 7-bromo-5,8-dimethoxy-1,2,3,4-tetrahydronaphthalen-2-amine; 5,7,8-trimethoxy-1,2,3,4-tetrahydronaphthalen-2-amine; or 5,6,8-trimethoxy-1,2,3,4-tetrahydronaphthalen-2-amine.

In embodiments, the present disclosure provides a compound of Formula (III-A):

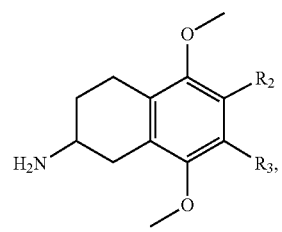

(III-A)

wherein $R_2$ and $R_3$ have definitions as provided herein.

In embodiments of the compounds of Formula (III), $R_1$ is methyl.

In embodiments of the compounds of Formula (III), $R_1$ is $C_2$-$C_6$ fluoroalkyl.

In embodiments of the compounds of Formula (III) or (III-A), $R_2$ is H.

In embodiments of the compounds of Formula (III) or (III-A), $R_2$ is halogen.

In embodiments of the compounds of Formula (III) or (III-A), $R_2$ is F, Cl, or I.

In embodiments of the compounds of Formula (III) or (III-A), $R_2$ is CN.

In embodiments of the compounds of Formula (III) or (III-A), $R_2$ is —S(O)(Y)$R_6$.

In embodiments of the compounds of Formula (III) or (III-A), $R_2$ is —S(O)$_2R_6$.

In embodiments of the compounds of Formula (III) or (III-A), $R_2$ is —S(O)$_2R_6$, wherein $R_6$ is H or $C_1$-$C_6$ alkyl.

In embodiments of the compounds of Formula (III) or (III-A), $R_2$ is —S(O)$_2R_6$, wherein $R_6$ is H or $C_1$-$C_3$ alkyl.

In embodiments of the compounds of Formula (III) or (III-A), $R_2$ is —S(O)$_2R_6$, wherein $R_6$ is H or $C_1$-$C_6$ fluoroalkyl.

In embodiments of the compounds of Formula (III) or (III-A), $R_2$ is —S(O)$_2R_6$, wherein $R_6$ is H or $C_1$-$C_3$ fluoroalkyl.

In embodiments of the compounds of Formula (III) or (III-A), $R_2$ is —S(O)$_2R_6$, wherein $R_6$ is $C_1$-$C_6$ alkyl or $C_1$-$C_6$ fluoroalkyl.

In embodiments of the compounds of Formula (III) or (III-A), $R_2$ is —S(O)(NH)$R_6$.

In embodiments of the compounds of Formula (III) or (III-A), $R_2$ is —S(O)(NH)$R_6$, wherein $R_6$ is H or $C_1$-$C_6$ alkyl.

In embodiments of the compounds of Formula (III) or (III-A), $R_2$ is —S(O)(NH)$R_6$, wherein $R_6$ is H or $C_1$-$C_3$ alkyl.

In embodiments of the compounds of Formula (III) or (III-A), $R_2$ is —S(O)(NH)$R_6$, wherein $R_6$ is H or $C_1$-$C_6$ fluoroalkyl.

In embodiments of the compounds of Formula (III) or (III-A), $R_2$ is —S(O)(NH)$R_6$, wherein $R_6$ is H or $C_1$-$C_3$ fluoroalkyl.

In embodiments of the compounds of Formula (III) or (III-A), $R_2$ is —S(O)(NH)$R_6$, wherein $R_6$ is $C_1$-$C_6$ alkyl or $C_1$-$C_6$ fluoroalkyl.

In embodiments of the compounds of Formula (III) or (III-A), $R_2$ is —S(O)$_2$H.

In embodiments of the compounds of Formula (III) or (III-A), $R_2$ is —S(O)(NH)H.

In embodiments of the compounds of Formula (III) or (III-A), $R_2$ is —S(O)$_2CH_3$.

In embodiments of the compounds of Formula (III) or (III-A), $R_2$ is —S(O)(NH)$CH_3$.

In embodiments of the compounds of Formula (III) or (III-A), $R_3$ is H.

In embodiments of the compounds of Formula (III) or (III-A), $R_3$ is halogen.

In embodiments of the compounds of Formula (III) or (III-A), $R_3$ is F, Cl, or I.

In embodiments of the compounds of Formula (III) or (III-A), $R_3$ is CN.

In embodiments of the compounds of Formula (III) or (III-A), $R_3$ is —S(O)(Y)$R_6$.

In embodiments of the compounds of Formula (III) or (III-A), $R_3$ is —S(O)$_2R_6$.

In embodiments of the compounds of Formula (III) or (III-A), $R_3$ is —S(O)$_2R_6$, wherein $R_6$ is H or $C_1$-$C_6$ alkyl.

In embodiments of the compounds of Formula (III) or (III-A), $R_3$ is —S(O)$_2R_6$, wherein $R_6$ is H or $C_1$-$C_3$ alkyl.

In embodiments of the compounds of Formula (III) or (III-A), $R_3$ is —S(O)$_2R_6$, wherein $R_6$ is H or $C_1$-$C_6$ fluoroalkyl.

In embodiments of the compounds of Formula (III) or (III-A), $R_3$ is —S(O)$_2R_6$, wherein $R_6$ is H or $C_1$-$C_3$ fluoroalkyl.

In embodiments of the compounds of Formula (III), $R_3$ is —S(O)$_2R_6$, wherein $R_6$ is $C_1$-$C_6$ alkyl or $C_1$-$C_6$ fluoroalkyl.

In embodiments of the compounds of Formula (III) or (III-A), $R_3$ is —S(O)(NH)$R_6$.

In embodiments of the compounds of Formula (III) or (III-A), $R_3$ is —S(O)(NH)$R_6$, wherein $R_6$ is H or $C_1$-$C_6$ alkyl.

In embodiments of the compounds of Formula (III) or (III-A), $R_3$ is —S(O)(NH)$R_6$, wherein $R_6$ is H or $C_1$-$C_3$ alkyl.

In embodiments of the compounds of Formula (III) or (III-A), $R_3$ is —S(O)(NH)$R_6$, wherein $R_6$ is H or $C_1$-$C_6$ fluoroalkyl.

In embodiments of the compounds of Formula (III) or (III-A), $R_3$ is —S(O)(NH)$R_6$, wherein $R_6$ is H or $C_1$-$C_3$ fluoroalkyl.

In embodiments of the compounds of Formula (III) or (III-A), $R_3$ is —S(O)(NH)$R_6$, wherein $R_6$ is $C_1$-$C_6$ alkyl or $C_1$-$C_6$ fluoroalkyl.

In embodiments of the compounds of Formula (III) or (III-A), $R_3$ is —S(O)$_2$H.

In embodiments of the compounds of Formula (III) or (III-A), $R_3$ is —S(O)(NH)H.

In embodiments of the compounds of Formula (III) or (III-A), $R_3$ is —S(O)$_2CH_3$.

In embodiments of the compounds of Formula (III) or (III-A), $R_3$ is —S(O)(NH)$CH_3$.

In embodiments of the compounds of Formula (III) or (III-A), $R_2$ and $R_3$ are H.

In embodiments of the compounds of Formula (III) or (III-A), $R_2$ and $R_3$ are independently H, $C_1$-$C_6$ alkyl, $C_1$-$C_6$ fluoroalkyl, halogen, CN, $OR_7$ or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ fluoroalkyl, halogen, CN, $OR_7$ or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ alkyl, $C_1$-$C_6$ fluoroalkyl, CN, $OR_7$ or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ alkyl, $C_1$-$C_6$ fluoroalkyl, halogen, $OR_7$ or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ alkyl, $C_1$-$C_6$ fluoroalkyl, halogen, CN, or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ alkyl, $C_1$-$C_6$ fluoroalkyl, halogen, CN, or $OR_7$, wherein at least one of $R_2$ and $R_3$ is H.

In embodiments of the compounds of Formula (III) or (III-A), $R_2$ and $R_3$ are independently H, halogen, CN, $OR_7$ or —S(O)(Y)$R_6$, wherein at least one of $R_2$ and $R_3$ is H.

In embodiments of the compounds of Formula (III) or (III-A), $R_2$ and $R_3$ are independently H, CN, $OR_7$ or —S(O)(Y)$R_6$, wherein at least one of $R_2$ and $R_3$ is H.

In embodiments of the compounds of Formula (III) or (III-A), $R_2$ and $R_3$ are independently H, $OR_7$ or —S(O)(Y)$R_6$, wherein at least one of $R_2$ and $R_3$ is H.

In embodiments of the compounds of Formula (III) or (III-A), $R_2$ and $R_3$ are independently H or —S(O)(Y)$R_6$, wherein at least one of $R_2$ and $R_3$ is H.

In embodiments of the compounds of Formula (III) or (III-A), $R_2$ and $R_3$ are independently H, $C_1$-$C_6$ alkyl, halogen, CN, or —S(O)(Y)$R_6$, wherein at least one of $R_2$ and $R_3$ is H.

In embodiments of the compounds of Formula (III) or (III-A), $R_2$ and $R_3$ are independently H, halogen, CN, or —S(O)(Y)$R_6$, wherein at least one of $R_2$ and $R_3$ is H.

In embodiments of the compounds of Formula (III), X is CH.

In embodiments of the compounds of Formula (III), X is N.

In embodiments of the compounds of Formula (III), $R_4$ is H.

In embodiments of the compounds of Formula (III), $R_5$ is H.

In embodiments of the compounds of Formula (III), $R_4$ and $R_5$ are each independently H.

In embodiments of the compounds of Formula (III) or (III-A), the compound has the following chemical formula:

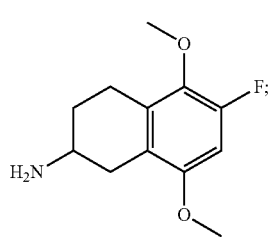

Compound (2-9)

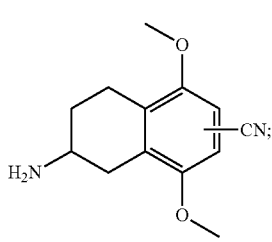

Compound (1-7)

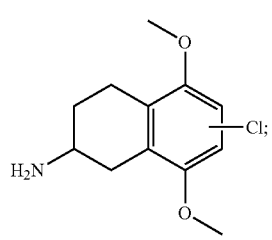

Compound (1-6)

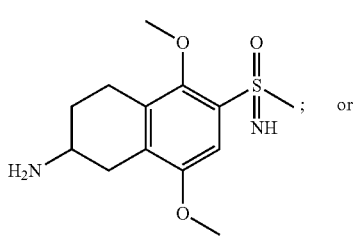

Compound (2-7)

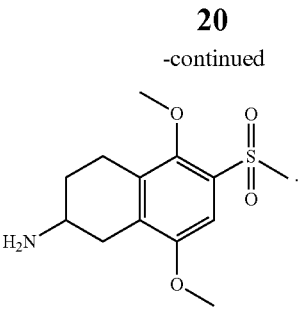

Compound (2-8)

Formula (IV):
In embodiments, the present disclosure provides compounds of Formula (IV):

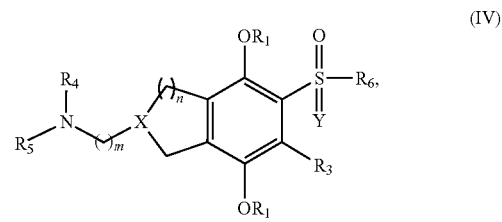

(IV)

or a pharmaceutically acceptable salt thereof; wherein,
$R_1$ is independently H, $C_1$-$C_6$ alkyl, or $C_1$-$C_6$ fluoroalkyl;
$R_3$ is H, $C_1$-$C_6$ alkyl, $C_1$-$C_6$ fluoroalkyl, halogen, CN, OR, or SRI;
$R_4$ and $R_5$ are independently H, $C_1$-$C_6$ alkyl, or $C_1$-$C_6$ fluoroalkyl;
$R_6$ and $R_7$ are independently H, $C_1$-$C_6$ alkyl, or $C_1$-$C_6$ fluoroalkyl;
X is CH or N;
m is 0, 1, 2 or 3; and
n is 0, 1, 2 or 3.

In embodiments, the present disclosure provides a compound of Formula (IV-A):

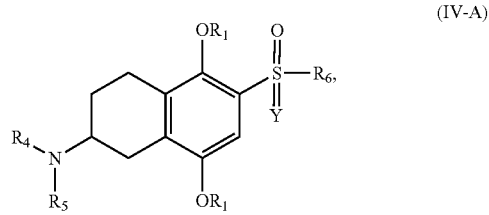

(IV-A)

wherein $R_1$, $R_4$, $R_5$, $R_6$, and Y have the definitions provided herein.

In embodiments of the compounds of Formula (IV) or (IV-A), Y is =O.

In embodiments of the compounds of Formula (IV) or (IV-A), Y is =NH.

In embodiments of the compounds of Formula (IV) or (IV-A), $R_1$ is $C_1$-$C_6$ alkyl.

In embodiments of the compounds of Formula (IV) or (IV-A), $R_1$ is $C_1$-$C_3$ alkyl.

In embodiments of the compounds of Formula (IV) or (IV-A), $R_1$ is methyl.

In embodiments of the compounds of Formula (IV) or (IV-A), $R_1$ is H.

In embodiments of the compounds of Formula (IV) or (IV-A), $R_1$ is $C_1$-$C_6$ fluoroalkyl.

In embodiments of the compounds of Formula (IV) or (IV-A), $R_1$ is independently $C_1$-$C_6$ alkyl or $C_1$-$C_6$ fluoroalkyl.

In embodiments of the compounds of Formula (IV) or (IV-A), $R_1$ is independently H or $C_1$-$C_6$ fluoroalkyl.

In embodiments of the compounds of Formula (IV) or (IV-A), $R_1$ is independently H or $C_1$-$C_6$ alkyl.

In embodiments of the compounds of Formula (IV) or (IV-A), $R_1$ is independently $C_1$-$C_3$ alkyl or $C_1$-$C_3$ fluoroalkyl.

In embodiments of the compounds of Formula (IV) or (IV-A), $R_1$ is independently H or $C_1$-$C_3$ fluoroalkyl.

In embodiments of the compounds of Formula (IV) or (IV-A), $R_1$ is independently H or $C_1$-$C_3$ alkyl.

In embodiments of the compounds of Formula (IV) or (IV-A), $R_1$ is independently H or methyl.

In embodiments of the compounds of Formula (IV), $R_3$ is H.

In embodiments of the compounds of Formula (IV), $R_3$ is halogen.

In embodiments of the compounds of Formula (IV), $R_3$ is I, Br, Cl, or F.

In embodiments of the compounds of Formula (IV), $R_3$ is $C_1$-$C_6$ alkyl, $C_1$-$C_6$ fluoroalkyl, halogen, CN, $OR_7$ or $SR_1$.

In embodiments of the compounds of Formula (IV), $R_3$ is H, $C_1$-$C_6$ fluoroalkyl, halogen, CN, $OR_7$ or $SR_1$.

In embodiments of the compounds of Formula (IV), $R_3$ is H, $C_1$-$C_6$ alkyl, halogen, CN, $OR_7$ or $SR_1$.

In embodiments of the compounds of Formula (IV), $R_3$ is H, $C_1$-$C_6$ alkyl, $C_1$-$C_6$ fluoroalkyl, CN, $OR_7$ or $SR_1$.

In embodiments of the compounds of Formula (IV), $R_3$ is H, $C_1$-$C_6$ alkyl, $C_1$-$C_6$ fluoroalkyl, $OR_7$ or $SR_1$.

In embodiments of the compounds of Formula (IV), $R_3$ is H, $C_1$-$C_6$ alkyl, $C_1$-$C_6$ fluoroalkyl, CN or $SR_1$.

In embodiments of the compounds of Formula (IV), $R_3$ is H, $C_1$-$C_6$ alkyl, $C_1$-$C_6$ fluoroalkyl, or CN.

In embodiments of the compounds of Formula (IV), $R_3$ is H, methyl, halogen, or CN.

In embodiments of the compounds of Formula (IV), $R_3$ is H, halogen, or CN.

In embodiments of the compounds of Formula (IV), $R_3$ is H, methyl, or halogen.

In embodiments of the compounds of Formula (IV), $R_3$ is H or methyl.

In embodiments of the compounds of Formula (IV), $R_3$ is H or halogen.

In embodiments of the compounds of Formula (IV) or (IV-A), $R_4$ and $R_5$ are independently H, methyl, ethyl or propyl.

In embodiments of the compounds of Formula (IV) or (IV-A), $R_4$ and $R_5$ are independently H or methyl.

In embodiments of the compounds of Formula (IV) or (IV-A), $R_4$ and $R_5$ are independently H or methyl.

In embodiments of the compounds of Formula (IV) or (IV-A), $R_6$ is $C_1$-$C_6$ alkyl or $C_1$-$C_6$ fluoroalkyl.

In embodiments of the compounds of Formula (IV) or (IV-A), $R_6$ is $C_1$-$C_3$ alkyl or $C_1$-$C_3$ fluoroalkyl.

In embodiments of the compounds of Formula (IV) or (IV-A), $R_6$ is H or $C_1$-$C_6$ alkyl.

In embodiments of the compounds of Formula (IV) or (IV-A), $R_6$ is H or $C_1$-$C_6$ fluoroalkyl.

In embodiments of the compounds of Formula (IV) or (IV-A), Reis H or $C_1$-$C_3$ alkyl.

In embodiments of the compounds of Formula (IV) or (IV-A), $R_6$ is H or $C_1$-$C_3$ fluoroalkyl.

In embodiments of the compounds of Formula (IV) or (IV-A), Reis $C_1$-$C_6$ alkyl.

In embodiments of the compounds of Formula (IV) or (IV-A), $R_6$ is $C_1$-$C_6$ fluoroalkyl.

In embodiments of the compounds of Formula (IV) or (IV-A), $R_6$ is $C_1$-$C_3$ alkyl.

In embodiments of the compounds of Formula (IV) or (IV-A), $R_6$ is $C_1$-$C_3$ fluoroalkyl.

In embodiments of the compounds of Formula (IV) or (IV-A), R is H.

In embodiments of the compounds of Formula (IV), X is CH.

In embodiments of the compounds of Formula (IV), X is N.

In embodiments of the compounds of Formula (IV), m is 0.

In embodiments of the compounds of Formula (IV), m is 1.

In embodiments of the compounds of Formula (IV), m is 2.

In embodiments of the compounds of Formula (IV), m is 3.

In embodiments of the compounds of Formula (IV), n is 0.

In embodiments of the compounds of Formula (IV), n is 1.

In embodiments of the compounds of Formula (IV), n is 2.

In embodiments of the compounds of Formula (IV), n is 3.

In embodiments of the compounds of Formula (IV) or (IV-A), the compound has the following chemical formula:

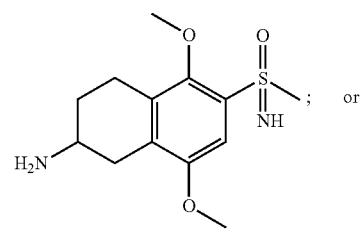

Compound (2-7)

or

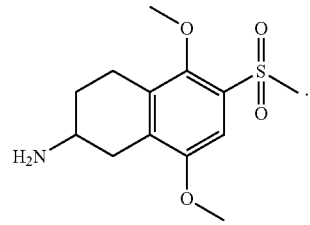

Compound (2-8)

In embodiments, the present disclosure provides compounds of the following chemical formulas:

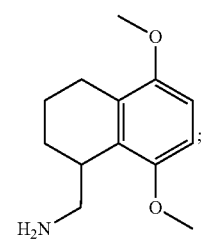

-continued

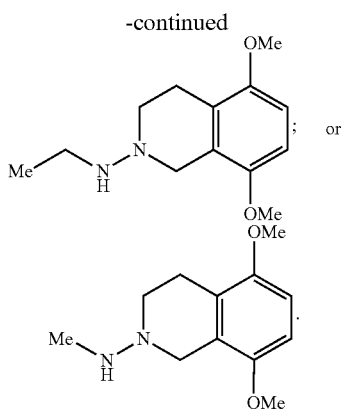

Compositions

In embodiments, the present disclosure provides a pharmaceutical composition comprising a therapeutically effective amounts of one or more compounds of the present disclosure (e.g., a compound of Formula (I), (I-A), (I-B), (II), (II-A), (II-B), (III), (III-A), (IV), (IV-A) (3-1), Table 1 or Table 2) or a pharmaceutically acceptable salt thereof and a pharmaceutically acceptable excipient is provided.

The pharmaceutically acceptable excipients and adjuvants are added to the composition or formulation for a variety of purposes. In embodiments, a pharmaceutical composition comprising one or more compounds disclosed herein, or a pharmaceutically acceptable salt thereof, further comprise a pharmaceutically acceptable carrier. In embodiments, a pharmaceutically acceptable carrier includes a pharmaceutically acceptable excipient, binder, and/or diluent. In embodiments, suitable pharmaceutically acceptable carriers include, but are not limited to, inert solid fillers or diluents and sterile aqueous or organic solutions. In embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods of Treatment

In one aspect, the compounds of the present disclosure are administered to a patient in need thereof to modulate a serotonin receptor, e.g., 5-HT2A receptor. In embodiments, the present disclosure provides methods of modulating serotonin receptor activity comprising administering a therapeutically effect amount of a compound of the present disclosure (e.g., a compound of Formula (I), (I-A), (I-B), (II), (II-A), (II-B), (III), (III-A), (IV), (IV-A) (3-1), Table 1 or Table 2) or a pharmaceutically acceptable salt thereof. In embodiments, modulating is activating or agonizing a serotonin receptor, e.g., 5-HT2A receptor. In embodiments, the subject is a human.

In embodiments, the present disclosure provides methods of treating a disease or disorder that is treatable by administration of a serotonin receptor agonist, e.g., 5-HT2A receptor agonist. In embodiments, the agonist is a partial agonist of the 5-HT2A receptor. In embodiments, the agonist is a full agonist of the 5-HT2A receptor.

In embodiments, the present disclosure provides methods of treating a mental health disease or disorder, the method comprising administering a therapeutically effective amount of a compound of the present disclosure (e.g., Formula (I), (I-A), (I-B), (II), (II-A), (II-B), (III), (III-A), (IV), (IV-A) (3-1), Table 1 or Table 2 or a pharmaceutically acceptable salt thereof).

In embodiments, the present disclosure provides methods of treating a mental health disease or disorder, the method comprising administering a pharmaceutical composition comprising a compound of the present disclosure (e.g., Formula (I), (I-A), (I-B), (II), (II-A), (II-B), (III), (III-A), (IV), (IV-A), (3-1), Table 1 or Table 2 or a pharmaceutically acceptable salt thereof) and a pharmaceutically acceptable excipient.

In embodiments, the mental health disease or disorder is selected from the group consisting of major depressive disorder, treatment resistant depression, substance use disorders and eating disorders. In embodiments, eating disorders include illnesses such as anorexia nervosa, bulimia nervosa, and other disorders related to eating (e.g., binge eating).

In embodiments, the mental health disease or disorder is an eating disorder.

In embodiments, the mental health disease or disorder is selected from the group consisting of compulsive disorders, anxiety disorders, stress disorders, and rumination.

In embodiments, the mental health disease or disorder is a mood disorder. In embodiments, mood disorders include e.g., depressive disorders, such as major depressive disorder or treatment resistant depression.

In embodiments, the mental health disorder is a substance abuse disorder. In embodiments, substance use related disorders are disorders of maladaptive patterns of substance use, and include criteria, such as recurrent substance use related problems, tolerance to a substance, withdrawal upon discontinuing use, an inability to cut down or control use of the substance, and giving up important social, occupational, or recreational activities because of using the substance. See e.g., the Diagnostic and Statistical Manual of Mental Disorders (DSM-5). In embodiments, the substance use related disorder is a disorder resulting from the use of: alcohol; caffeine; cannabis; hallucinogens (such as phencyclidine or similarly acting arylcyclohexylamines, and other hallucinogens, such as LSD); inhalants; opioids; sedatives, hypnotics, or anxiolytics; stimulants (including amphetamine-type substances, cocaine, and other stimulants); tobacco; and other substances.

Numbered Embodiments of the Disclosure

In addition to the disclosure above, the Examples below, and the appended claims, the disclosure sets for the following numbered embodiments.

Provided below are embodiments related to compounds of Formula (I) and (II).

1. A compound of Formula (I):

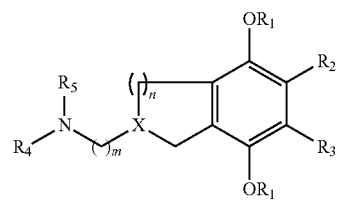

or a pharmaceutically acceptable salt thereof; wherein,
$R_1$, is independently H, $C_1$-$C_6$ alkyl, $C_1$-$C_6$ fluoroalkyl;
$R_2$, and $R_3$, are independently H, $C_1$-$C_6$ alkyl, $C_1$-$C_6$ fluoroalkyl, halogen, CN, $OR_1$ or $SR_1$;

$R_4$ and $R_5$ are independently H, $C_1$-$C_6$ alkyl, $C_1$-$C_6$ fluoroalkyl;

X is C or N;

m is 0, 1, 2 or 3;

n is 0, 1, 2 or 3;

wherein the compound is not 5,8-dimethoxy-6-methyl-1,2,3,4-tetrahydronaphthalen-2-amine; 5,8-dimethoxy-1,2,3,4-tetrahydronaphthalen-2-amine; 5,8-dimethoxy-N-methyl-1,2,3,4-tetrahydronaphthalen-2-amine; or (5,8-dimethoxy-1,2,3,4-tetrahydronaphthalen-2-yl) methanamine.

2. The compound of embodiment 1, wherein $R_1$ is independently $C_1$-$C_6$ alkyl.

3. The compound of any one of embodiments 1-2, wherein $R_1$ is methyl.

4. The compound of any one of embodiments 1-3, wherein $R_2$ and $R_3$ are independently H or $C_1$-$C_6$ alkyl.

5. The compound of any one of embodiments 1-3, wherein $R_2$ and $R_3$ are independently H, methyl or ethyl.

6. The compound of any one of embodiments 1-3, wherein $R_2$ and $R_3$ are independently H or $C_1$-$C_6$ fluoroalkyl.

7. The compound of any one of embodiments 1-3, wherein $R_2$ and $R_3$ are independently H or trifluoromethyl.

8. The compound of any one of embodiments 1-3, wherein $R_2$ and $R_3$ are independently H, F, Cl, Br, I or CN.

9. The compound of any one of embodiments 1-3, wherein $R_2$ and $R_3$ are independently H or halogen.

10. The compound of any one of embodiments 1-3, wherein $R_2$ and $R_3$ are independently H or I.

11. The compound of any one of embodiments 1-10, wherein $R_4$ and $R_5$ are independently H, methyl, ethyl or propyl.

12. The compound of any one of embodiments 1-10, wherein $R_4$ and $R_5$ are independently H or methyl.

13. The compound of any one of embodiments 1-10, wherein $R_4$ is H.

14. The compound of any one of embodiments 1-10, wherein $R_4$ is methyl.

15. The compound of any one of embodiments 1-10, wherein $R_4$ is ethyl.

16. The compound of any one of embodiments 1-15, wherein $R_5$ is H.

17. The compound of any one of embodiments 1-16, wherein X is CH.

18. The compound of any one of embodiments 1-16, wherein X is N.

19. The compound of any one of embodiments 1-18, wherein m is 0.

20. The compound of any one of embodiments 1-18, wherein m is 1.

21. The compound of any one of embodiments 1-20, wherein n is 2.

22. The compound of embodiment 1, having the following chemical formula:

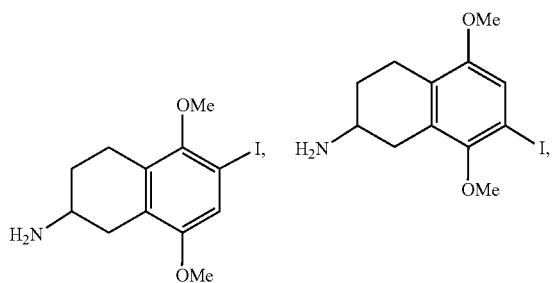

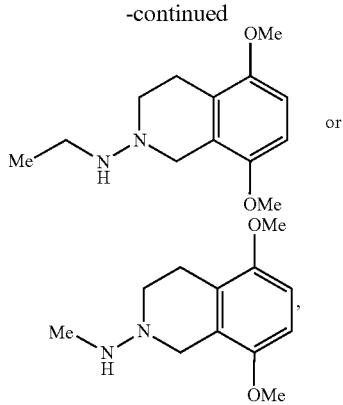

or a pharmaceutically acceptable salt thereof.

23. A compound of Formula (II):

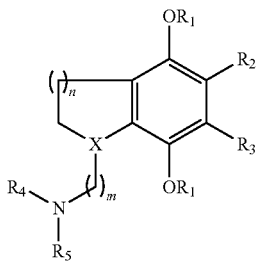

or a pharmaceutically acceptable salt thereof, wherein, $R_1$ is independently H, $C_1$-$C_6$ alkyl, $C_1$-$C_6$ fluoroalkyl;

$R_2$, and $R_3$, are independently H, $C_1$-$C_6$ alkyl, $C_1$-$C_6$ fluoroalkyl, halogen, CN, $OR_1$ $S(O)NHR_1R_2$, or $SR_1$;

$R_4$ and $R_5$ are independently H, $C_1$-$C_6$ alkyl, $C_1$-$C_6$ fluoroalkyl;

X is C or N;

m is 0, 1, 2 or 3;

n is 0, 1, 2 or 3;

wherein the compound is not (5,8-dimethoxy-1,2,3,4-tetrahydronaphthalen-1-yl) methanamine.

24. The compound of embodiment 23, wherein $R_1$ is independently $C_1$-$C_6$ alkyl.

25. The compound of embodiment 23, wherein $R_1$ is methyl.

26. The compound of any one of embodiments 23-25, wherein $R_2$ and $R_3$ are independently H or $C_1$-$C_6$ alkyl.

27. The compound of any one of embodiments 23-25, wherein $R_2$ and $R_3$ are independently H, methyl or ethyl.

28. The compound of any one of embodiments 23-25, wherein $R_2$ and $R_3$ are independently H or $C_1$-$C_6$ fluoroalkyl.

29. The compound of any one of embodiments 23-25, wherein $R_2$ and $R_3$ are independently H or trifluoromethyl.

30. The compound of any one of embodiments 23-25, wherein $R_2$ and $R_3$ are independently H, F, Cl, Br, I or CN.

31. The compound of any one of embodiments 23-25, wherein $R_2$ and $R_3$ are independently H or halogen.

32. The compound of any one of embodiments 23-25, wherein $R_2$ and $R_3$ are independently H or I.

33. The compound of any one of embodiments 23-32, wherein $R_4$ and $R_5$ are independently H, methyl, ethyl or propyl.

34. The compound of any one of embodiments 23-32, wherein $R_4$ and $R_5$ are independently H or methyl.

35. The compound of any one of embodiments 23-32, wherein $R_4$ is H.

36. The compound of any one of embodiments 23-32, wherein $R_4$ is methyl.

37. The compound of any one of embodiments 23-32, wherein $R_4$ is ethyl.

38. The compound of any one of embodiments 23-32, wherein $R_5$ is H.

39. The compound of any one of embodiments 23-38, wherein X is CH.

40. The compound of any one of embodiments 23-38, wherein X is N.

41. The compound of any one of embodiments 23-38, wherein m is 0.

42. The compound of any one of embodiments 23-38, wherein m is 1.

43. The compound of any one of embodiments 23-42, wherein n is 2.

44. A pharmaceutical composition, comprising a compound of any one of embodiments 1-43 and a pharmaceutically acceptable excipient.

45. A method of treating a mental health disease or disorder, the method comprising administering a therapeutically effective amount of a compound of any one of embodiments 1-43 or the pharmaceutical composition of embodiment 44.

46. The method of embodiment 45, wherein the mental health disease or disorder is selected from the group consisting of major depressive disorder, treatment resistant depression, substance use disorders and eating disorders.

47. The method of embodiment 45, wherein the mental health disease or disorder is selected from the group consisting of compulsive disorders, anxiety disorders, stress disorders, and rumination.

Provided below are embodiments related to compounds of Formula (III) and (IV).

1. A compound of Formula (III):

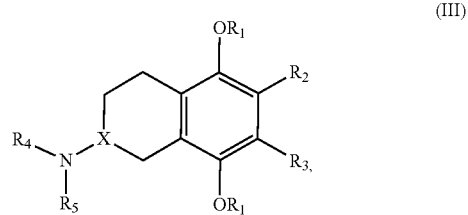

(III)

or a pharmaceutically acceptable salt thereof; wherein,
$R_1$ is independently methyl or $C_2$-$C_6$ fluoroalkyl;
$R_2$ and $R_3$ are independently H, $C_1$-$C_6$ alkyl, $C_1$-$C_6$ fluoroalkyl, halogen, CN, $OR_7$ or —S(O)(Y)$R_6$;
Y is —O or =NH;
$R_4$ and $R_5$ are independently H or $C_1$-$C_6$ fluoroalkyl;
$R_6$ and $R_7$ are independently H, $C_1$-$C_6$ alkyl, or $C_1$-$C_6$ fluoroalkyl; and
X is CH or N;
wherein the compound is not 5,8-dimethoxy-6-methyl-1,2,3,4-tetrahydronaphthalen-2-amine; 5,8-dimethoxy-1,2,3,4-tetrahydronaphthalen-2-amine; 6-bromo-5,8-dimethoxy-1,2,3,4-tetrahydronaphthalen-2-amine; 7-bromo-5,8-dimethoxy-1,2,3,4-tetrahydronaphthalen-2-amine; 5,7,8-trimethoxy-1,2,3,4-tetrahydronaphthalen-2-amine; or 5,6,8-trimethoxy-1,2,3,4-tetrahydronaphthalen-2-amine.

2. The compound of embodiment 1, wherein R is methyl.

3. The compound of embodiment 1, wherein $R_1$ is $C_2$-$C_6$ fluoroalkyl.

4. The compound of any one of embodiments 1-3, wherein $R_2$ is H.

5. The compound of any one of embodiments 1-3, wherein $R_2$ is a halogen.

6. The compound of any one of embodiments 1-3, wherein $R_2$ is F, Cl, or I.

7. The compound of any one of embodiments 1-3, wherein $R_2$ is CN.

8. The compound of any one of embodiments 1-3, wherein $R_2$ is —S(O)$_2$$R_6$.

9. The compound of any one of embodiments 1-3, wherein $R_2$ is —S(O)(NH)$R_6$.

10. The compound of any one of embodiments 1-9, wherein $R_3$ is H.

11. The compound of any one of embodiments 1-9, wherein $R_3$ is a halogen.

12. The compound of any one of embodiments 1-9, wherein $R_3$ is F, Cl, or I.

13. The compound of any one of embodiments 1-9, wherein $R_3$ is CN.

14. The compound of any one of embodiments 1-9, wherein $R_3$ is —S(O)$_2$$R_6$.

15. The compound of any one of embodiments 1-9, wherein $R_3$ is —S(O)(NH)$R_6$.

16. The compound of any one of embodiments 1-9, wherein $R_2$ and $R_3$ are H.

17. The compound of any one of embodiments 1-16, wherein X is CH.

18. The compound of any one of embodiments 1-16, wherein X is N.

19. The compound of any one of embodiments 1-18, wherein $R_4$ is H.

20. The compound of any one of embodiments 1-19, wherein $R_5$ is H.

21. The compound of any one of embodiments 1-20, wherein $R_4$ and $R_5$ are each independently H.

22. The compound of any one of embodiments 1-21, having the following chemical formula:

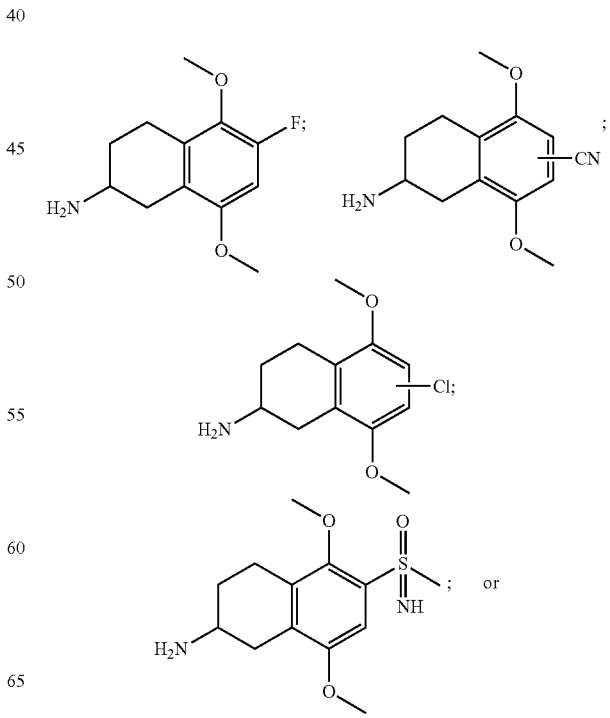

-continued

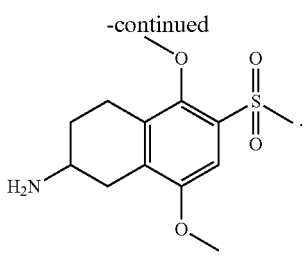

23. A compound of Formula (IV):

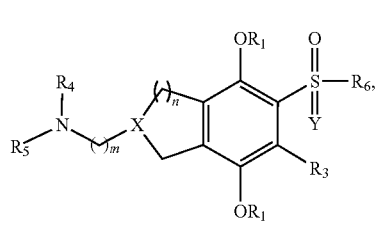

or a pharmaceutically acceptable salt thereof; wherein,
$R_1$ is independently H, $C_1$-$C_6$ alkyl, or $C_1$-$C_6$ fluoroalkyl;
$R_3$ is H, $C_1$-$C_6$ alkyl, $C_1$-$C_6$ fluoroalkyl, halogen, CN, $OR_7$ or $SR_1$;
$R_4$ and $R_5$ are independently H, $C_1$-$C_6$ alkyl, or $C_1$-$C_6$ fluoroalkyl;
$R_6$ and $R_7$ are independently H, $C_1$-$C_6$ alkyl, or $C_1$-$C_6$ fluoroalkyl;
X is CH or N;
m is 0, 1, 2 or 3; and
n is 0, 1, 2 or 3.

24. The compound of embodiment 23, wherein Y is =O.
25. The compound of embodiment 23, wherein Y is =NH.
26. The compound of any one of embodiments 23-25, wherein $R_1$ is $C_1$-$C_6$ alkyl.
27. The compound of any one of embodiments 23-25, wherein $R_1$ is $C_1$-$C_3$ alkyl.
28. The compound of any one of embodiments 23-25, wherein $R_1$ is methyl.
29. The compound of any one of embodiments 23-25, wherein $R_1$ is H.
30. The compound of any one of embodiments 23-25, wherein $R_1$ is $C_1$-$C_6$ fluoroalkyl.
31. The compound of any one of embodiments 23-30, wherein $R_3$ is H.
32. The compound of any one of embodiments 23-30, wherein $R_3$ is halogen.
33. The compound of any one of embodiments 23-32, wherein $R_4$ is H.
34. The compound of any one of embodiments 23-32, wherein $R_4$ is $C_1$-$C_6$ alkyl.
35. The compound of any one of embodiments 23-34, wherein $R_5$ is H.
36. The compound of any one of embodiments 23-34, wherein $R_5$ is $C_1$-$C_6$ alkyl.
37. The compound of any one of embodiments 23-34, wherein $R_4$ and $R_5$ are H.
38. The compound of any one of embodiments 23-37, wherein X is CH.
39. The compound of any one of embodiments 23-37, wherein X is N.
40. The compound of any one of embodiments 23-40, wherein m is 0.
41. The compound of any one of embodiments 23-40, wherein m is 1.
42. The compound of any one of embodiments 23-41, wherein n is 1.
43. The compound of any one of embodiments 23-41, wherein n is 2.
44. The compound of any one of embodiments 23-43, wherein $R_6$ is H.
45. The compound of any one of embodiments 23-43, wherein $R_6$ is $C_1$-$C_6$ alkyl.
46. The compound of any one of embodiments 23-43, wherein $R_6$ is $C_1$-$C_3$ alkyl.
47. A compound selected from:

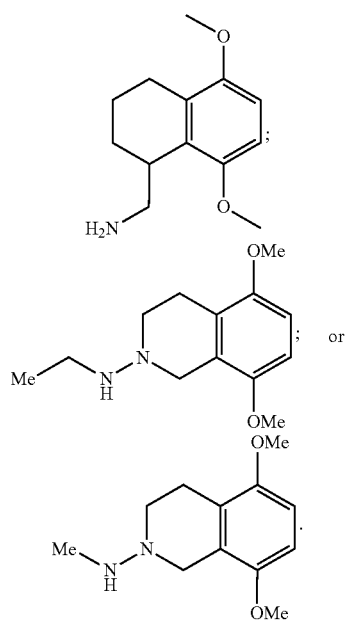

48. A pharmaceutical composition, comprising a compound of any one of embodiments 1-47 and a pharmaceutically acceptable excipient.
49. A method of treating a mental health disease or disorder, the method comprising administering a therapeutically effective amount of a compound of any one of embodiments 1-47 or the pharmaceutical composition of embodiment 48.
50. The method of embodiment 49, wherein the mental health disease or disorder is selected from the group consisting of major depressive disorder, treatment resistant depression, substance use disorders and eating disorders.
51. The method of embodiment 49, wherein the mental health disease or disorder is selected from the group consisting of compulsive disorders, anxiety disorders, stress disorders, and rumination.

EXAMPLES

Abbreviations dppf: 1,1'-bis(diphenylphosphino)ferrocene
dba: dibenzylideneacetone or dibenzalacetone General Methods of Preparing the Compounds of the Present Disclosure The following schemes provide methods for preparing the compounds of the present disclosure.

Unless otherwise noted, all materials/reagents were obtained from commercial suppliers and used without further purification. Reactions were monitored by LC-MS and/or thin layer chromatography (TLC) on silica gel 60 F254 (0.2 mm) pre-coated aluminum foil or glass-backed and visualized using UV light. $^1$HNMR (400 MHz) spectra was recorded on Broker spectrometers at RT with TMS or the residual solvent peak as the internal standard. Chemical shifts are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened). Preparative HPLC purifications were performed on Shimadzu LC-6AD. All purification work was completed using a Shim-pack PREP-DDS(H)KIT Column. The mobile phases were water (with 0.1% $HCO_2H$) and acetonitrile; all reagents used were of HPLC grade. The flow rate was 10 ml/min. LC-MS analyses were performed on Shimadzu LCMS-2020 equipped with LC-20AD or 30AD pumps, SPD-M20A PDA and Alltech 3300 ELSD; Mobile Phase: A:Water (0.1% Formic acid), B: ACN; 5 minute run; Column: Sepax BR-C18 4.6*50 mm, 3 um; Flow Rate: 1.0 ml/min; Oven Temperature: 40° C.; Gradient: 20% B for 0.2 min, increase to 70% B within 1.8 min, 70% B for 2.8 min, back to 20% B within 0.2 min, 20% B for 2 min). Preparative TLC was performed on Whatman LK6F Silica Gel 60A size 20×20 cm plates with a thickness of 1000 μm or equivalent.

Example 1: Preparation of 6-iodo-5,8-dimethoxy-1,2,3,4-tetrahydronaphthalen-2-amine/7-iodo-5,8-dimethoxy-1,2,3,4-tetrahydronaphthalen-2-amine

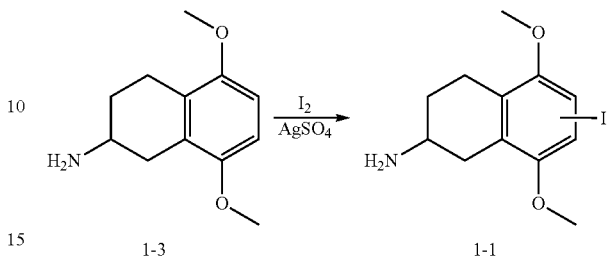

To a stirred solution of 5,8-dimethoxy-1,2,3,4-tetrahydronaphthalen-2-amine (100 mg, 0.41 mmol, 1.0 eq), $Ag_2SO_4$ (192 mg, 0.615 mmol, 1.5 eq) in MeOH (8 mL) was added $I_2$ (157 mg, 0.615 mmol, 1.5 eq). The resulting mixture was stirred at RT overnight. The reaction mixture was quenched with aqueous sodium bicarbonate and extracted with ethyl acetate. The organic layer was dried over anhydrous sodium sulfate and concentrated under reduced pressure to give a crude product which was purified by preparative-HPLC to afford the title compound which was converted to its TFA salt (40 mg, 25%) as a brown solid. LCMS: (ES$^+$): m/z 334.0 [M+H]$^+$. $^1$H NMR (400 MHz, DMSO-d6) δ 8.08 (s, 3H), 7.16 (s, 1H), 3.76 (dd, J=4.4 Hz, 3H), 3.63 (dd, J=2 Hz 2H), 3.18 (m, 1H), 2.95 (m, 1H), 2.75 (m, 1H), 2.65 (m, 1H), 2.05 (m, 1H), 1.65 (m, 1H).

Example 2: Preparation of 5,8-dimethoxy-6-methyl-1,2,3,4-tetrahydronaphthalen-2-amine (1-2)

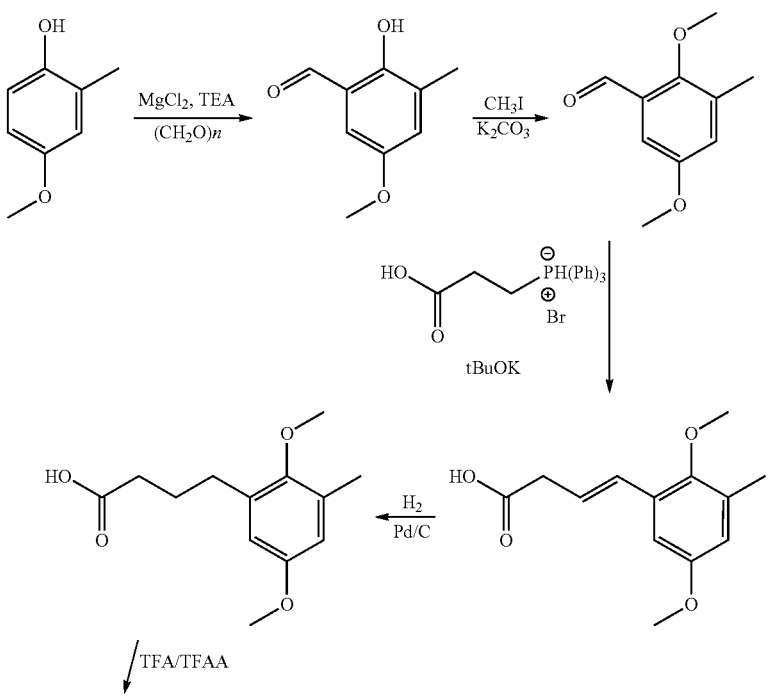

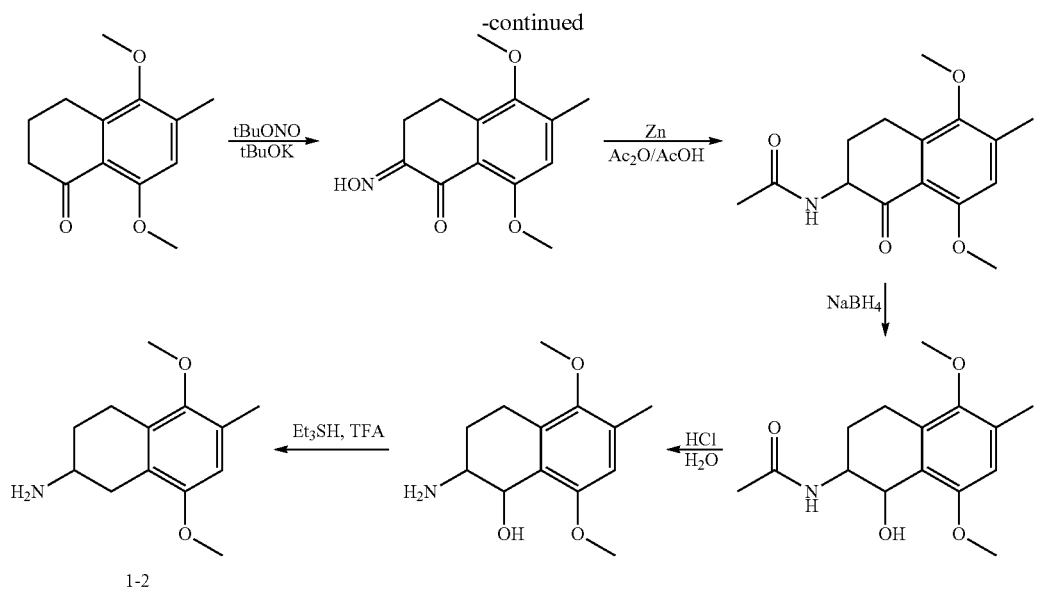

1-2

Step 1: Preparation of 2-hydroxy-5-methoxy-3-methylbenzaldehyde

A solution of 4-methoxy-2-methylphenol (4.6 g, 33.3 mmol, 1.0 eq), $MgCl_2$ (5.0 g, 50.0 mmol, 1.5 eq), $(CH_2O)_n$ (3.3 g, 110.0 mmol, 3.2 eq) and TEA (5.0 g, 50.0 mmol, 1.5 eq) in ACN (25 mL) was stirred at 85° C. for 2~3 hours. The reaction mixture was cooled to RT and poured into ice-water (200 mL), the resulting mixture was adjusted to pH=3 with hydrochloric acid (4 N) and extracted with EA. The organic layer was washed with water and brine, dried over $Na_2SO_4$, filtered and concentrated to give a crude product which was purified through silica gel column chromatography (petroleum ether:EA=95:5) to afford the title compound (5.0 g, 80%) as a yellow solid. $^1H$ NMR (400 MHZ, Solvent: $CDCl_3$) ppm 10.94 (s, 1H), 9.84 (s, 1H), 7.02-7.03 (d, J=3.2 Hz, 1H), 6.83-6.84 (d, J=3.2, 1H), 3.80 (s, 3H), 2.26 (s, 3H).

Step 2: Preparation of 2,5-dimethoxy-3-methylbenzaldehyde

A solution of 2-hydroxy-5-methoxy-3-methylbenzaldehyde (5.0 g, 30.0 mmol, 1.0 eq), $CH_3I$ (8.5 g, 60.0 mmol, 2.0 eq) and $K_2CO_3$ (10.0 g) in DMF (20 mL) was stirred at RT overnight. The TLC was monitored until the starting material was consumed. The reaction mixture was poured into water (30 mL) and extracted with MTBE (50 mL×3). The combined organic extracts were washed with water (25 mL), brine (25 mL), dried over $Na_2SO_4$ and concentrated to give a crude product which was purified by silica gel column chromatography (petroleum ether:EA=95:5) to afford the title product EGX-9-1-2 (5.2 g, 90%) as a yellow solid. $^1H$ NMR (400 MHZ, Solvent: $CDCl_3$) ppm 10.35 (s, 1H), 7.14-7.15 (d, J 3.2 Hz, 1H), 7.01-7.02 (d, J 3.2, 1H), 3.84 (s, 3H), 3.80 (s, 3H), 2.31 (s, 3H).

Step 3: Preparation of (E)-4-(2,5-dimethoxy-3-methylphenyl)but-3-enoic acid

To a solution of 2,5-dimethoxy-3-methylbenzaldehyde (2.4 g, 13.3 mmol) in THF (40 mL) was added (2-carboxyethyl)triphenylphosphonium (8.3 g, 20 mmol, 1.5 eq) and t-BuOK solution in THF (40 mL, 40 mmol, 3 eq) at 0° C. The reaction mixture was stirred at RT overnight. The solvent was removed, the residue was diluted with water, basified with sodium hydroxide and extracted with EtOAc (50 mL). The aqueous phase was adjusted to pH=2 with aqueous hydrochloric acid and extracted with DCM (30 mL×3). The combined organic extracts were washed with water (25 mL), brine (25 mL), dried over $Na_2SO_4$, filtered and concentrated to give the crude product (4.48 g) which was used in the next step without further purification.

Step 4: Preparation of 4-(2,5-dimethoxy-3-methylphenyl)butanoic acid

To a solution of (E)-4-(2,5-dimethoxy-3-methylphenyl)but-3-enoic acid (4.48 mg, 13.2 mmol) in MeOH (20 mL) was added Pd/C (250 mg) at RT and the reaction mixture was stirred overnight. The suspension was filtered and the filtrate was concentrated to afford the crude product which was used in next step without further purification (3.88 g, 100%).

Step 5: Preparation of 5,8-dimethoxy-6-methyl-3,4-dihydronaphthalen-1(2H)-one To a solution of 4-(2,5-dimethoxy-3-methylphenyl)butanoic acid (3.88 g, 13.3 mmol) in TFA (10 mL) was added TFAA (8.5 mL, 66.6 mmol, 5 eq) at RT and the reaction mixture was stirred overnight. The reaction was diluted with EtOAc and washed with water (25 mL), brine (25 mL), dried over $Na_2SO_4$, filtered and concentrated to give a crude product which was purified by silica gel chromatography (petroleum ether:EtOAc=5:1) to afford the title compound as a colorless oil (1.2 g, 56%).

Step 6: Preparation of (E)-2-(hydroxyimino)-5,8-dimethoxy-6-methyl-3,4-ihydronaphthalen-1(2H)-one To a solution of 5,8-dimethoxy-6-methyl-3,4-dihydronaphthalen-1(2H)-one (1.2 g, 5.45 mmol) in t-BuOH/$Et_2O$ (10 mL/10 mL) was added t-BuOK (911 mg, 8.12 mmol, 1.5 eq) and tert-butyl nitrite (843 mg, 8.12 mmol, 1.5 eq) at RT and the reaction mixture was stirred overnight. The reaction was quenched with water (25 mL), adjusted to pH=2 with aqueous hydrochloric acid and extracted with DCM (30 mL×3). The combined organic extracts were washed with water (25 mL), brine (25 mL), dried over $Na_2SO_4$, filtered and concentrated to give a crude product which was purified by silica gel chromatography (DCM:MeOH=100:1) to afford the title compound as a yellow solid (700 mg, 51%).

Step 7: Preparation of N-(5,8-dimethoxy-6-methyl-1-oxo-1,2,3,4-tetrahydronaphthalen-2-yl)acetamide To a solution of (E)-2-(hydroxyimino)-5,8-dimethoxy-6-methyl-3,4-dihydronaphthalen-1(2H)-one (500 mg, 2.27 mmol, 1.3 eq) in AcOH (6 mL) was added Zn (445 mg, 6.81 mmol, 3 eq) and $Ac_2O$ (4 mL) at RT under $N_2$ and the reaction mixture was stirred overnight. The suspension was filtered, the filtrate diluted with water, adjusted to pH=8 with sodium hydroxide (4 M in water) and extracted with EtOAc. The extract was washed with water (25 mL), brine (25 mL), dried over $Na_2SO_4$, filtered, and concentrated to give a crude product which was purified by silica gel chromatography (DCM:MeOH=100:1) to afford the title compound as a colorless oil (180 mg, 40%).

Step 8: Preparation of N-(1-hydroxy-5,8-dimethoxy-6-methyl-1,2,3,4-etrahydronaphthalen-2-yl)acetamide To a solution of N-(5,8-dimethoxy-6-methyl-1-oxo-1,2,3,4-tetrahydronaphthalen-2-yl)acetamide (184 mg, 0.664 mmol) in MeOH (10 mL) was added $NaBH_4$ (76 g, 2.0 mmol, 3 eq) at 0° C. The reaction mixture was stirred at RT overnight. The reaction was diluted with EtOAc, washed with water (25 mL), brine (25 mL), dried over $Na_2SO_4$, filtered and concentrated to give the crude product which was used in next step without further purification (203 mg, 100%).

Step 9: Preparation of 2-amino-5,8-dimethoxy-6-methyl-1,2,3,4-tetrahydronaphthalen-1-ol To a solution of N-(1-hydroxy-5,8-dimethoxy-6-methyl-1,2,3,4-tetrahydronaphthalen-2-yl)-acetamide (158 mg, 0.565 mmol) in $H_2O$ (5 mL) was added concentrated hydrochloric acid (12 M in water, 0.8 mL) at RT. The reaction mixture was stirred at reflux for 2 h, cooled to room temperature and adjusted to pH=8 with sodium hydroxide (4 M in water). The reaction mixture was extracted with EtOAc. The organic layer was washed with water (25 mL), brine (25 mL), dried over $Na_2SO_4$, filtered and concentrated to give the crude product which was used in next step without further purification (143 mg, 56%). $^1H$ NMR (400 MHZ, methanol-$d_4$) δ 6.74 (s, 1H), 5.03 (dd, J 3.7, 1.3 Hz, 1H), 3.85 (s, 3H), 3.69 (s, 3H), 3.38-3.34 (m, 1H), 3.16-3.10 (m, 1H), 2.76-2.67 (m, 1H), 2.30 (s, 3H), 2.14-2.04 (m, 1H), 1.99-1.92 (m, 1H).

Step 10: Preparation of 5,8-dimethoxy-6-methyl-1,2,3,4-tetrahydronaphthalen-2-amine To a solution of 2-amino-5,8-dimethoxy-6-methyl-1,2,3,4-tetrahydronaphthalen-1-ol (80 mg, 0.33 mmol) in TFA (6 mL) was added $Et_3SiH$ (206 mg, 1.65 mmol, 5 eq) at RT and the reaction mixture was stirred. The reaction was diluted with water (25 mL), adjust to pH=10 with sodium hydroxide (4 M in water). The reaction mixture was extracted with EtOAc. The organic layer was washed with water, brine (25 mL each), dried over $Na_2SO_4$, filtered and concentrated to give a crude product which was purified by silica gel chromatography (DCM:MeOH=100:1) to afford the title compound as a colorless oil (64 mg, 86%). $^1H$ NMR (400 MHZ, methanol-$d_4$) δ 6.65 (s, 1H), 3.80 (s, 3H), 3.69 (s, 3H), 3.50 (m, 1H), 3.19 (dd, J 17.2 Hz, 6.0 Hz, 1H), 3.06 (dt, J 17.5, 4.8 Hz, 1H), 2.81 (m, 1H), 2.53 (dd) 16.8, 9.8 Hz, 1H), 2.28 (s, 3H), 2.25-2.14 (m, 1H), 1.90-1.65 (m, 1H).

Example 3: Preparation of 5,8-dimethoxy-1,2,3,4-tetrahydronaphthalen-2-amine hydro-chloride (1-3)

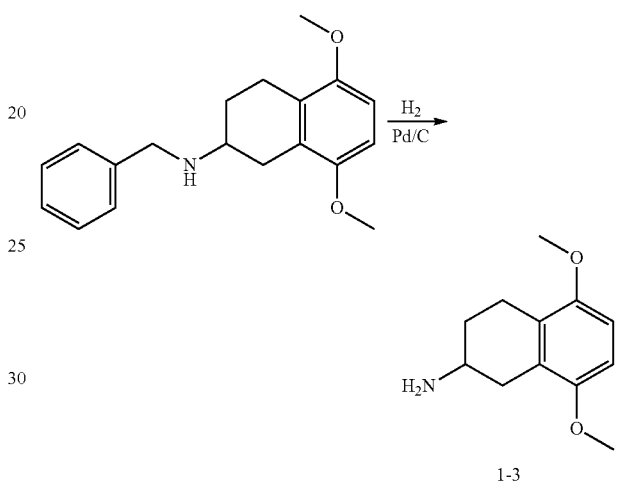

To a solution of N-benzyl-5,8-dimethoxy-1,2,3,4-tetrahydronaphthalen-2-amine (3.92 mg, 13.2 mmol) in MeOH (20 mL) was added $Pd(OH)_2/C$ (400 mg) at RT and the resulting mixture was stirred overnight. The suspension was filtered and the filtrate was concentrated to afford a crude product which was dissolved in MTBE (5 mL) and treated with 4M HCl in dioxane (5 mL, 19.8 mmol, 1.5 eq) at RT. The resulting mixture was stirred at room temperature for 2 h. The suspension was filtered to afford the title compound as a white solid (2.25 g, 78%). LCMS: (ES−): m/z 208.3 [M+H]$^+$. $^1H$ NMR (400 MHZ, DMSO-$d_6$) δ 8.31 (s, 2H), 6.75 (s, 2H), 3.73 (s, 3H), 3.71 (s, 3H), 3.14-3.01 (m, 1H), 2.90-2.80 (m, 1H), 2.55-2.44 (m, 1H), 2.18-2.04 (m, 1H), 1.66 (qd, J=11.7, 5.5 Hz, 1H).

Example 4: Preparation of 5,8-dimethoxy-N-methyl-1,2,3,4-tetrahydronaphthalen-2-amine hydro-chloride (1-4)

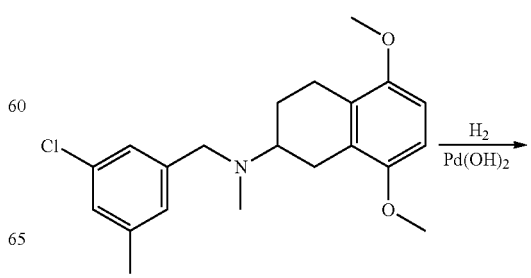

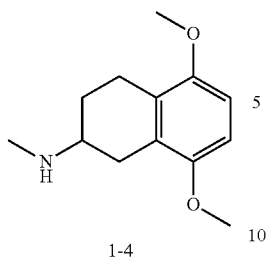

1-4

A suspension of N-(3-chloro-5-methylbenzyl)-5,8-dimethoxy-N-methyl-1,2,3,4-tetrahydro-naphthalen-2-amine (100 mg, 0.322 mmol, 1.0 eq) and Pd(OH)$_2$ (10 mg, 10%) in MeOH (5 mL) was stirred at RT under H$_2$ overnight. The reaction was monitored by TLC until the reaction was complete. The Pd(OH)$_2$ was filtered, and the filtered cake was washed with MeOH twice. The combined organic layers were concentrated under reduced pressure to give a crude residue which was purified by silica gel flash column chromatography (eluted with DCM/MeOH=15:1 gradient) to afford the title compound as the free base (30 mg, 42%) which was converted to the HCl salt (35 mg, 42%) as a white solid after treatment with HCl in dioxane. LCMS: m/z 222.35 [M+H]$^+$. $^1$H NMR (400 MHZ, DMSO) δ 9.03 (s, 2H), 6.76 (s, 2H), 3.74 (s, 3H), 3.72 (s, 3H), 3.12 (dd, J=17.3, 5.1 Hz, 1H), 2.92-2.81 (m, 1H), 2.61 (s, 3H), 2.55 (d, J=10.8 Hz, 1H), 2.52 (d, J=1.9 Hz, 1H), 2.44 (s, 1H), 2.26-2.16 (m, 1H), 1.65 (qd, J=11.6, 5.5 Hz, 1H).

Example 5: Preparation of 6-bromo-5,8-dimethoxy-1,2,3,4-tetrahydronaphthalen-2-amine/7-bromo-5,8-dimethoxy-1,2,3,4-tetrahydronaphthalen-2- amine

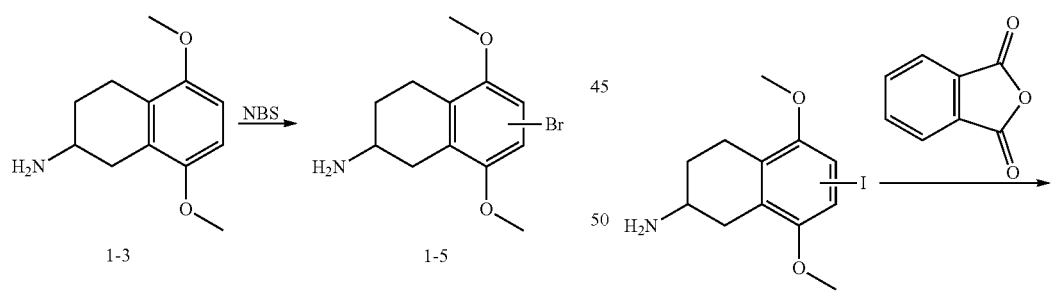

1-3    1-5

To a solution of 5,8-dimethoxy-1,2,3,4-tetrahydronaphthalen-2-amine hydrobromide (200 mg, 1.735 mmol, 1 eq) in DCM (5 mL) was added NBS (386 mg, 2.17 mmol, 1.25 eq) at RT and the resulting mixture was stirred overnight. The reaction was quenched with water and extracted with EA (50 ml×3). The combined organic extracts were washed with brine, dried over Na$_2$SO$_4$, filtered and concentrated to give a crude product which was purified by silica gel chromatography (DCM:MeOH=100:1) to afford the title compound (46 mg, 23%) as a colorless oil. LCMS: 1.867 min, m/z 287.90 [M+H]$^+$ $^1$H NMR (400 MHZ, Methanol-d$_4$) δ 7.00 (s, 1H), 3.82-3.72 (m, 6H), 3.55-3.45 (m, 1H), 3.29-3.02 (m, 1H), 2.96-2.76 (m, 1H), 2.76-2.44 (m, 2H), 2.25-2.15 (m, 1H), 1.85-1.71 (m, 1H).

Example 6: Preparation of 6-chloro-5,8-dimethoxy-1,2,3,4-tetrahydronaphthalen-2-amine/7-chloro-5,8-dimethoxy-1,2,3,4-tetrahydronaphthalen-2-amine

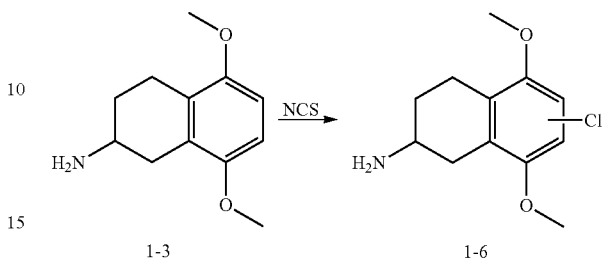

1-3    1-6

To a solution of 5,8-dimethoxy-1,2,3,4-tetrahydronaphthalen-2-amine hydrochloride (200 mg, 0.82 mmol, 1 eq) in DCM (5 mL) was added NCS (132 mg, 0.985 mmol, 1.2 eq) at RT and the resulting mixture was stirred overnight. The reaction was quenched with water, and extracted with EA (50 mL×3). The combined organic extracts were washed with brine, dried over Na$_2$SO$_4$, filtered and concentrated to give a crude product which was purified by silica gel chromatography (DCM:MeOH=100:1) to afford the title compound (41 mg, 20%) as a colorless oil. LCMS: 1.952 min, m/z 241.50 [M+H]$^+$ $^1$H NMR (400 MHZ, Methanol-d$_4$) δ 6.85 (s, 1H), 3.85-3.69 (m, 6H), 3.59-3.44 (m, 1H), 3.28-3.02 (m, 1H), 2.99-2.75 (m, 1H), 2.76-2.46 (m, 2H), 2.26-2.15 (m, 1H), 1.86-1.70 (m, 1H).

Example 7: Preparation of 6-amino-1,4-dimethoxy-5,6,7,8-tetrahydronaphthalene-2-carbonitrile/6-amino-1,4-dimethoxy-5,6,7,8-tetrahydronaphthalene-3-carbonitrile (2-6)

1-1

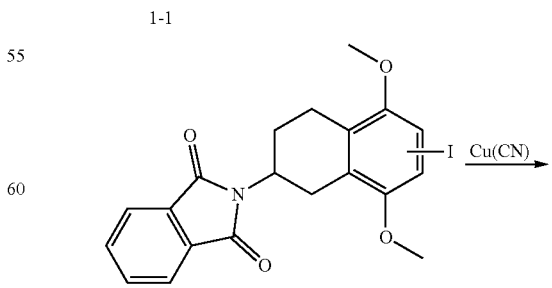

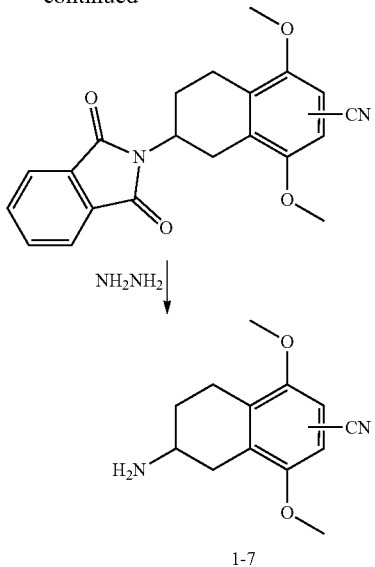

Step 1: Preparation of 2-(6-iodo-5,8-dimethoxy-1,2,3,4-tetrahydronaphthalen-2-yl)isoindoline-1,3-dione/2-(7-iodo-5,8-dimethoxy-1,2,3,4-tetrahydronaphthalen-2-yl)isoindoline-1,3-dione A solution of 6-iodo-5,8-dimethoxy-1,2,3,4-tetrahydronaphthalen-2-amine/7-iodo-5,8-dimethoxy-1,2,3,4-tetrahydronaphthalen-2-amine (400 mg, 1.20 mmol. 1 eq), isobenzofuran-1,3-dione (220 mg, 1.44 mmol, 1.2 eq) and $Et_3N$ (266 mg, 2.6 mmol, 2.2 eq) in 20 mL toluene was heated to 110° C. under $N_2$ for 16 h. The reaction mixture was washed with water and extracted with EA. The organic phase was collected and concentrated under reduced pressure to afford the crude product which was purified by flash chromatography (eluting with petroleum ether:EA=3:1) to afford the title compound (380 mg, 68%). $^1H$ NMR (400 MHZ, Solvent: $CDCl_3$) ppm 7.90-7.80 (m, 2H), 7.77-7.69 (m, 2H), 7.04 (d, J=4.7 Hz, 1H), 4.55-4.42 (m, 1H), 3.75 (dd, J=18.1, 15.6 Hz, 6H), 3.44 (dd, J=16.3, 11.7 Hz, 1H), 3.25-3.16 (m, 1H), 3.12-2.91 (m, 2H), 2.79 (dd, J=20.6, 8.7 Hz, 1H), 2.62 (dd, J=13.4, 5.5 Hz, 2H), 2.01 (d, J=5.5 Hz, 1H).

Step 2: Preparation of 6-amino-1,4-dimethoxy-5,6,7,8-tetrahydronaphthalene-2-carbonitrile/6-amino-1,4-dimethoxy-5,6,7,8-tetrahydronaphthalene-3-carbonitrile A solution of 2-(6-iodo-5,8-dimethoxy-1,2,3,4-tetrahydronaphthalen-2-yl)isoindoline-1,3-dione/2-(7-iodo-5,8-dimethoxy-1,2,3,4-tetrahydronaphthalen-2-yl)isoindoline-1,3-dione (380 mg, 0.82 mmol, 1 eq) in DMF was added CuCN (90 mg, 1 mmol, 1.2 eq) and the reaction was heated to 150° C. under $N_2$ for 16 h. The reaction mixture was washed with water and extracted with DCM. The organic phase was collected and concentrated under reduced pressure to afford the crude product which was purified by flash chromatography (eluting with petroleum ether:EA=1:1) to afford the title compound (200 mg, 67%).

Step 3: 6-amino-1,4-dimethoxy-5,6,7,8-tetrahydronaphthalene-2-carbonitrile/6-amino-1,4-dimethoxy-5,6,7,8-tetrahydronaphthalene-3-carbonitrile A solution of 6-(1,3-dioxoisoindolin-2-yl)-1,4-dimethoxy-5,6,7,8-tetrahydronaphthalene-2/3-carbonitrile (200 mg, 0.8 mmol, 1 eq) and hydrazine (200 mg, 2 mmol, 2.5 eq) in EtOH (2 mL) was heated to 80° C. under $N_2$ for 15 min. The reaction mixture was washed with water and extracted by DCM. The organic phase was collected and concentrated under reduced pressure to afford the crude product which was purified by flash chromatography (eluting with DCM:MeOH=10:1) to afford the title compound (100 mg, 50%).

Example 8: Synthesis of (5,8-dimethoxy-1,2,3,4-tetrahydronaphthalen-1-yl)methanamine (3-1)

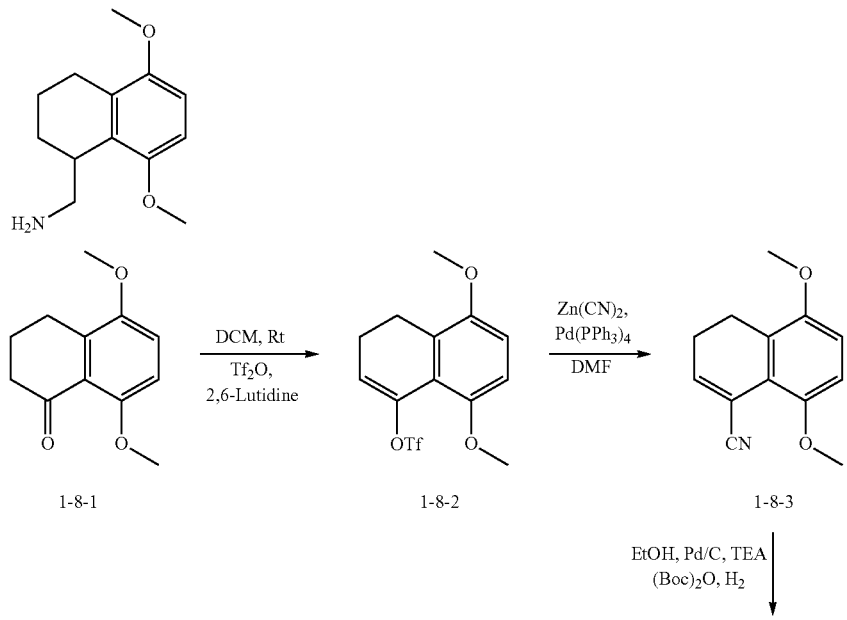

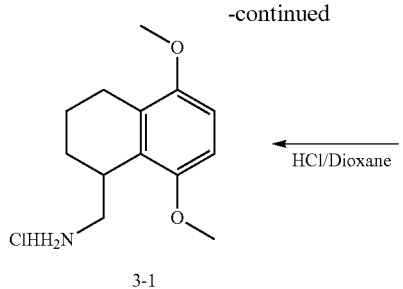
3-1

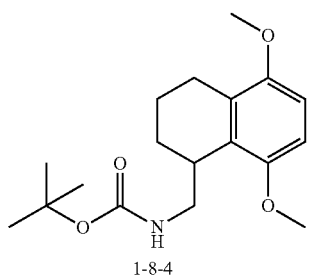
1-8-4

Step 1: Synthesis of intermediate 1-8-2: 5,8-dimethoxy-3,4-dihydronaphthalen-1-yl trifluoromethanesulfonate A suspension of 5,8-dimethoxy-3,4-dihydronaphthalen-1(2H)-one (1.0 g, 4.8 mmol, 1.0 eq) and 2,6-dimethylpyridine (778 g, 7.2 mmol, 1.5 eq) in DCM (20 mL) was stirred at 0° C. for 30 min. Tf$_2$O (1.1 g, 7.2 mmol, 1.5 eq) was slowly added to the mixture. The resulting mixture was stirred at RT overnight. The organic phase was concentrated under reduced pressure to give a crude residue which was purified by silica gel flash chromatography (eluted with petroleum ether/EA=10:1 gradient) to afford the title compound EGX-19-3-1 as an oil (1.0 g, 61%).

Step 2: Synthesis of intermediate 1-8-3: 5,8-dimethoxy-3,4-dihydronaphthalene-1-carbonitrile A suspension of 5,8-dimethoxy-3,4-dihydronaphthalen-1-yl trifluoromethane-sulfonate (500 mg, 1.47 mmol, 1.0 eq), Zn(CN)$_2$ (190 mg, 1.62 mmol, 1.1 eq) and Pd(PPh$_3$)$_4$ (84 mg, 0.07 mmol, 0.05 eq) in DMF (8 mL) was heated to 75° C. overnight. The organic phase was concentrated under reduced pressure to give a crude residue which was purified by silica gel flash column chromatography (eluted with petroleum ether/EA=15:1 gradient) to afford the title compound EGX-19-3-2 (100 mg, 32%).

Step 3: Synthesis of intermediate 1-8-4: tert-butyl ((5,8-dimethoxy-1,2,3,4-tetrahydro naphthalen-1-yl)methyl)carbamate A suspension of 5,8-dimethoxy-3,4-dihydronaphthalene-1-carbonitrile (70 mg, 0.32 mmol, 1.0 eq), TEA (98.5 mg, 0.97 mmol, 3 eq), (Boc)$_2$O (212 mg, 0.97 mmol, 3 eq) and Pd/C (10 mg) in EtOH (10 mL) was stirred under H$_2$ at RT overnight. The reaction mixture was filtered. The organic phase was concentrated under reduced pressure to give a crude residue which was purified by silica gel flash chromatography (eluted with petroleum ether/EA=50:1 gradient) to afford the title compound as a white solid, EGX-19-3-3 (90 mg, 87%).

Step 4: Synthesis of final product 3-1: (5,8-dimethoxy-1,2,3,4-tetrahydronaphthalen-1-yl)methanamine hydrochloride A suspension of tert-butyl ((5,8-dimethoxy-1,2,3,4-tetrahydronaphthalen-1-yl)methyl)carbamate (90 mg, 0.28 mmol, 1.0 eq) in EA (10 mL) was stirred at RT and HCl/Dioxane (0.5 mL) was added to the solution. The reaction was monitored by TLC until the reaction was complete. The solvent was concentrated under reduced pressure to afford the title compound EGX-19-6 (60 mg, 83%) as a white solid.

LCMS: 0.941 min, m/z 222.30 [M+H], $^1$H NMR (400 MHZ, MeOD) δ 6.77 (s, 2H), 3.82 (s, 3H), 3.75 (s, 3H), 3.33-3.31 (m, 1H), 3.19-3.15 (m, 1H), 2.98-2.92 (m, 1H), 2.91 (m, 1H), 2.48-2.38 (m, 1H), 1.99 (m, 1H), 1.88-1.85 (m, 2H).

Example 9: GPCR Arrestin Assay

Arrestin Pathway (Performed by DiscoverX Eurofins)

The PathHunter® β-Arrestin assay monitors the activation of a GPCR in a homogenous, non-imaging assay format using a technology developed by DiscoverX called Enzyme Fragment Complementation (EFC) with β-galactosidase (β-Gal) as the functional reporter. The enzyme is split into two inactive complementary portions (EA for Enzyme Acceptor and PK for ProLink) expressed as fusion proteins in the cell. EA is fused to β-Arrestin and PK is fused to the GPCR of interest. When the GPCR is activated and β-Arrestin is recruited to the receptor, ED and EA complementation occurs, restoring β-Gal activity which is measured using chemiluminescent PathHunter® Detection Reagents.

PathHunter cell lines (DiscoveRx Eurofins) were expanded from freezer stocks according to standard procedures. Human 5-HT2A receptor-mediated GPCR β-arrestin activity was evaluated in stably transfected human-derived U2OS cells. Cells were seeded in a total volume of 20 μL into white walled, 384-well microplates and incubated at 37° C. overnight prior to testing.

For agonist determination, cells were incubated with sample to induce response. Intermediate dilution of sample stocks was performed to generate 5× sample in assay buffer. 5 μL of 5× sample was added to cells and incubated at 37° C. or room temperature for 120 minutes. Vehicle concentration was 1%.

β-Arrestin assay signal was generated through a single addition of 12.5 or 15 μL (50% v/v) of PathHunter Detection reagent cocktail, followed by a one hour incubation at room temperature. Microplates were read following signal generation with a PerkinElmer Envision™ instrument for chemiluminescent signal detection.

Compound activity was analyzed using CBIS data analysis suite (ChemInnovation, CA). For agonist mode assays, percentage activity was calculated using the following formula:

$$\% \text{ Activity} = 100\% \times (\text{mean } RLU \text{ of test sample} - \text{mean } RLU \text{ of vehicle control})/$$
$$(\text{mean MAX control ligand} - \text{mean } RLU \text{ of vehicle control}).$$

In these studies, the MAX control ligand response was generated using 1 µM serotonin.

Calcium Mobilization Assay Method (Performed by DiscoveRx Eurofins)

The Calcium No-WashPLUS assay monitors the activation of a GPCR via Gq secondary messenger signaling in a live cell, non-imaging assay format. Calcium mobilization in PathHunter® cell lines or other cell lines stably expressing Gq-coupled GPCRs is monitored using a calcium-sensitive dye that is loaded into cells. GPCR activation by a compound results in the release of calcium from intracellular stores and an increase in dye fluorescence that is measured in real-time.

Cell lines expressing the GPCR of interest were expanded from freezer stocks according to standard procedures. Human 5-HT2A, 5-HT2B or 5-HT2C receptor-mediated calcium mobilization was evaluated in stably transfected human-derived U2OS (5-HT2A or 5-HT2B) or HEK (5-HT2B) cells. Cells were seeded in a total volume of 20 µL into black-walled, clear-bottom, Poly-D-lysine coated 384-well microplates and incubated at 37° C. overnight prior to testing.

Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 µL Dye Loading Buffer. Cells were incubated for 45 minutes at room temperature.

For agonist determination, cells were incubated with sample to induce response. After dye loading, cells were removed from the incubator and 10 µL HBSS/20 mM Hepes was added. 3× vehicle was included in the buffer when performing agonist dose curves to define the EC80 for subsequent antagonist assays. Cells were incubated for 30 minutes at room temperature in the dark to equilibrate plate temperature.

Intermediate dilution of sample stocks was performed to generate 4× sample in assay buffer. Compound agonist activity was measured on a FLIPR Tetra (MDS). Calcium mobilization was monitored for 2 minutes and 10 µL 4× sample in HBSS/20 mM Hepes was added to the cells 5 seconds into the assay.

Compound activity data was analyzed using CBIS data analysis suite (ChemInnovation, CA). For agonist mode assays, percentage activity is calculated using the following formula:

$$\% \text{ Activity} = 100\% \times (\text{mean } RFU \text{ of test sample} - \text{mean } RFU \text{ of vehicle control})/$$
$$(\text{mean MAX control ligand} - \text{mean } RFU \text{ of vehicle control}).$$

In these studies, the MAX RFU was generated by using 0.1 µM serotonin for the calcium mobilization assay.

CAMP Secondary Messenger Pathway Assay Method (Performed by DiscoveRx Eurofins)

DiscoverX has developed a panel of cell lines stably expressing non-tagged GPCRs that signal through cAMP. Hit Hunter® CAMP assays monitor the activation of a GPCR via Gi and Gs secondary messenger signaling in a homogenous, non-imaging assay format using a technology developed by DiscoverX called Enzyme Fragment Complementation (EFC) with β-galactosidase (β-Gal) as the functional reporter. The enzyme is split into two complementary portions: EA for Enzyme Acceptor and ED for Enzyme Donor. ED is fused to CAMP and in the assay competes with cAMP generated by cells for binding to a cAMP-specific antibody. Active β-Gal is formed by complementation of exogenous EA to any unbound ED-cAMP. Active enzyme can then convert a chemiluminescent substrate, generating an output signal detectable on a standard microplate reader.

cAMP Hunter cell lines were expanded from freezer stocks according to standard procedures. Human 5-HT1A receptor-mediated cAMP signaling was evaluated in stably transfected hamster-derived CHO cells. Cells were seeded in a total volume of 20 µL into white walled, 384-well microplates and incubated at 37° C. overnight. cAMP modulation was determined using the DiscoverX HitHunter CAMP XS+ assay.

For Gi agonist determination, cells were incubated with sample in the presence of EC80 (15 mM) forskolin to induce response. Media was aspirated from cells and replaced with 10 µL HBSS/10 mM Hepes. Intermediate dilution of sample stocks was performed to generate 4× sample in assay buffer containing 4× EC80 forskolin. 5 µL of 4× sample was added to cells and incubated at 37° C. for 30 minutes. Final assay vehicle concentration was 1%. After compound incubation, assay signal was generated through incubation with 20 µL cAMP XS+ ED/CL lysis cocktail for one hour followed by incubation with 20 µL cAMP XS+ EA reagent for three hours at room temperature. Microplates were read following signal generation with a PerkinElmer Envision™ instrument for chemiluminescent signal detection.

Compound activity was analyzed using CBIS data analysis suite (ChemInnovation, CA). For Gi agonist mode assays, percentage activity is calculated using the following formula: % Activity=100%×(1−(mean RLU of test sample−mean RLU of MAX control)/(mean RLU of vehicle control−mean RLU of MAX control)). In these studies, the MAX RLU was generated by using 1 µM serotonin.

Biological Experiments

Compounds (2-1), (1-1), (2-2), (2-3), (1-4), (1-5), (2-4) and (3-1) were assessed for biological activity across a panel of 5-HT receptors including 5-HT2A, 5-HT2B, 5-HT2C and 5-HT1A. Biased signaling was assessed by monitoring both intracellular Gq-mediated calcium release, as well as β-arrestin activation and recruitment to the GPCR. The results are shown in Table 3 below.

All available data for the compounds in this series

TABLE 3

| EC50 values measured for Compounds (1-2) and (1-1) across a panel of 5-HT receptors | | |
|---|---|---|
| 5-HT Receptor assessed | $EC_{50}$ (nM) Compound (1-1) | $EC_{50}$ (nM) Compound (1-2) |
| 5-HT1A (Gi signaling) | 369 | 438 |
| 5-HT2A (Gq signaling) | 8.8 | 38.8 |
| 5-HT2B (Gq signaling) | >10,000 | 315 |
| 5-HT2C (Gq signaling) | 5.6 | 4.8 |
| 5-HT2A (β-arrestin signaling) | 120 | 386 |
| 5-HT1A (β-arrestin signaling) | >10000 | Not available |

The 2-aminotetralins studied displayed greater potency for the 5-HT2C receptor compared to the other 5-HT receptors studied (Tables 1 and 2). However, Compound (1-1) maintained near equipotency across both 5-HT2A and 5-HT2C. Interestingly, Compound (1-1) demonstrated >1136-fold increase in potency at 5-HT2A compared to 5-HT2B (FIG. 1A). Substitution of the 6-iodo with 6-methyl, to afford Compound (1-2), yielded a reduced potency of only ~8-fold for 5-HT2A over 5-HT2B (FIG. 1A). Modulation of selectivity by such a small molecular change is surprising and unexpected given the structural similarity between the 5-HT2A and 5-HT2B receptors. Moreover, the superior selectivity afforded by Compound (1-1) has distinct safety advantages over Compound (1-2) and other non-selective psychedelics by potentially decreasing the risk of cardiac valvulopathy associated with prolonged 5-HT2B activation typically encountered upon repeated dosing of known 5-HT2B agonists such as fenphen (combination of fenfluramine/phentermine). The 2-aminotetralins studied afforded sub-micromolar potencies for 5HT1A. In comparison to psilocin, 2-aminotetralins were ~5-fold more potent for 5-HT1A. Given the importance of the 5-HT1A contribution to the psychedelic experience (Pokorny et al., 2016; Carter et al., 2005), 5-HT1A activation afforded by 2-aminotetralins may be therapeutically advantageous.

Figure 1B:
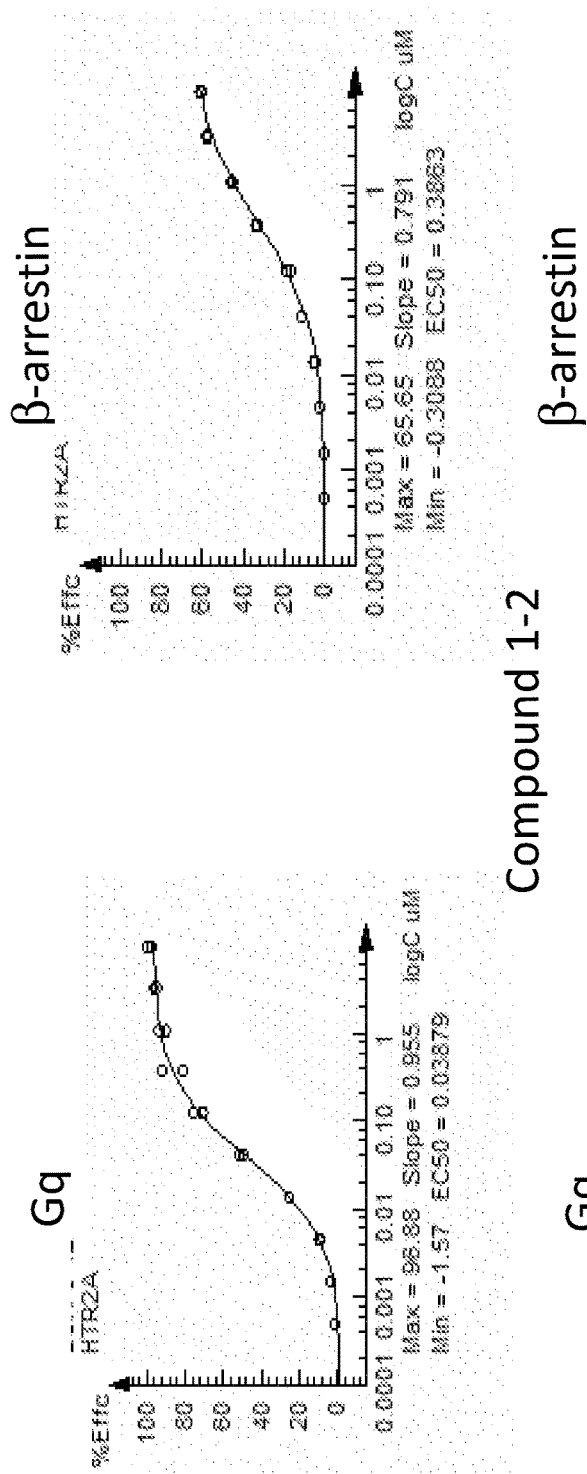
FIG. 1B shows EC50 profiles of Compounds 1-2 and 1-1, for comparing Gq and β-arrestin biased signaling pathways.
Figure 1B:
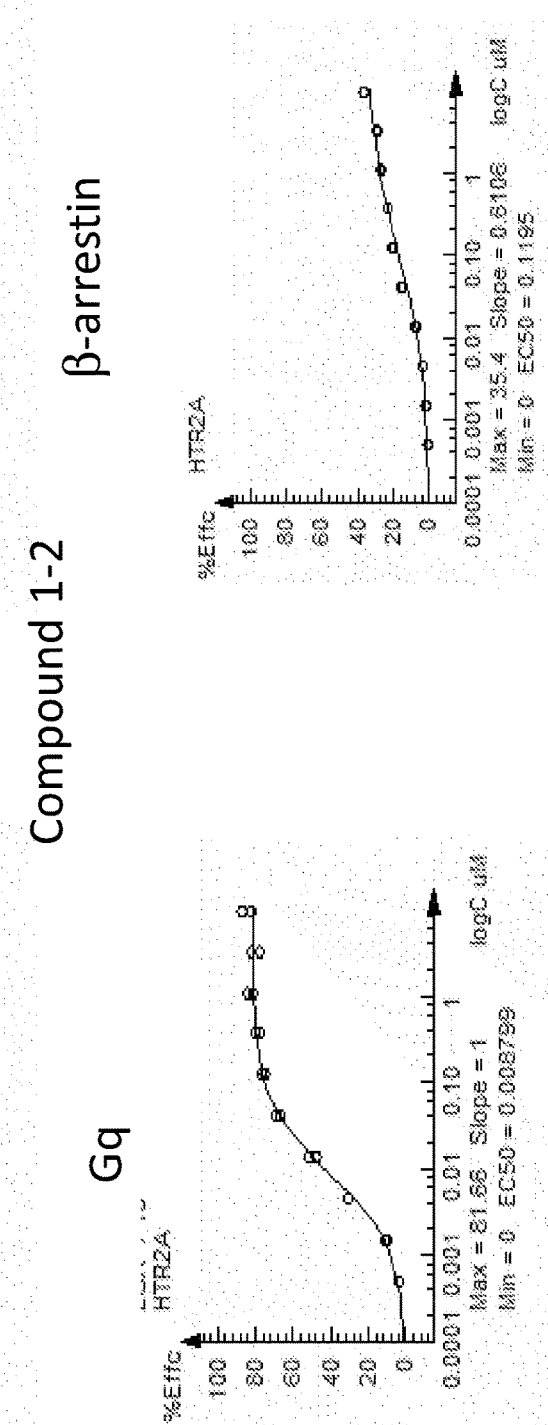

While the 2-aminotetralins studied were potent activators of 5-HT2A Gq-mediated signaling, these compounds had higher potency values for β-arrestin recruitment at 5-HT2A (FIG. 1B). Compound (1-1) was observed to maintain a 14-fold potency bias compared to ~10-fold for Compound (1-2). Such a bias may be important to uncoupling the psychedelic experiences of disassociation and hallucination from the therapeutic benefit.

The $EC_{50}$ profiles of the compounds demonstrated that all were agonists of 5-HT2A mediated signaling. However, while Compound (1-2) displayed full-agonism of 5-HT2A Gq-mediated signaling (97% max activation), Compound (1-1) showed reduced efficacy with a max activation of 82% (FIG. 1A) when compared to the maximum serotonin response. Both Compounds (1-2) and (1-1) exhibited partial agonism with maximum efficacy levels of 66% and 35%, respectively. These results suggest a potential for 5-HT2A Gq-mediated signaling bias for the compounds prepared and studied.

What is claimed:

1. A compound of Formula (III):

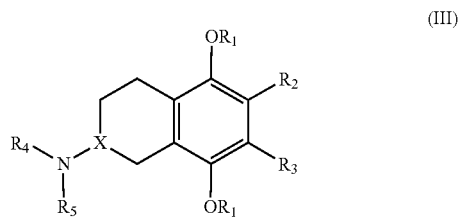

(III)

or a pharmaceutically acceptable salt thereof; wherein,
$R_1$ is methyl;
$R_2$ and $R_3$ are independently H, $C_1$-$C_6$ alkyl, halogen, CN, or $OR_7$;
$R_4$ and $R_5$ are H;
$R_7$ is H, $C_1$-$C_6$ alkyl, or $C_1$-$C_6$ fluoroalkyl; and
X is CH or N;
wherein the compound is not 5,8-dimethoxy-6-methyl-1,2,3,4-tetrahydronaphthalen-2-amine; 5,8-dimethoxy-1,2,3,4-tetrahydronaphthalen-2-amine; 6-bromo-5,8-dimethoxy-1,2,3,4-tetrahydronaphthalen-2-amine; 7-bromo-5,8-dimethoxy-1,2,3,4-tetrahydronaphthalen-2-amine; 5,7,8-trimethoxy-1,2,3,4-tetrahydronaphthalen-2-amine;
or 5,6,8-trimethoxy-1,2,3,4-tetrahydronaphthalen-2-amine.

2. The compound of claim 1, wherein $R_2$ is H, F, Cl, I, or CN.

3. The compound of claim 1, wherein $R_3$ is H, F, Cl, I, or CN.

4. A compound of Formula (IV):

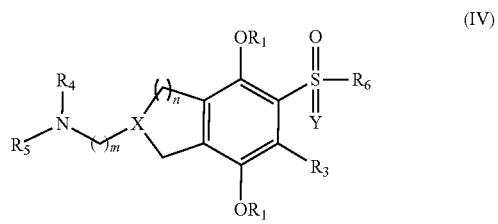

(IV)

or a pharmaceutically acceptable salt thereof; wherein,
$R_1$ is independently H or $C_1$-$C_6$ alkyl;
$R_3$ is H, $C_1$-$C_6$ alkyl, halogen, CN, $OR_7$ or $SR_1$;
$R_4$ and $R_5$ are independently H or $C_1$-$C_6$ alkyl;
$R_6$ and $R_7$ are independently H or $C_1$-$C_6$ alkyl;
X is CH or N;
Y is =O or =NH;
m is 0, 1, 2 or 3; and
n is 0, 1, 2 or 3.

5. The compound of claim 4, wherein Y is =O.
6. The compound of claim 4, wherein $R_1$ is $C_1$-$C_6$ alkyl.
7. The compound of claim 4, wherein $R_3$ is H or halogen.
8. The compound of claim 4, wherein $R_4$ is H or $C_1$-$C_6$ alkyl.
9. The compound of claim 4, wherein $R_5$ is H or $C_1$-$C_6$ alkyl.
10. The compound of claim 4, wherein X is CH.
11. The compound of claim 4, wherein m is 0 or 1.
12. The compound of claim 4, wherein n is 1 or 2.
13. The compound of claim 4, wherein $R_6$ is H or methyl.
14. A compound selected from:

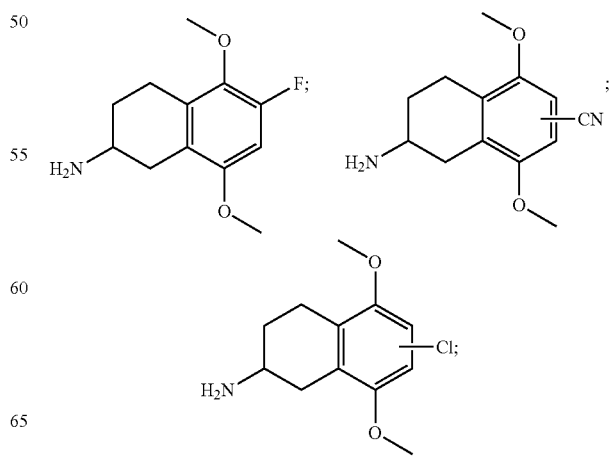

-continued

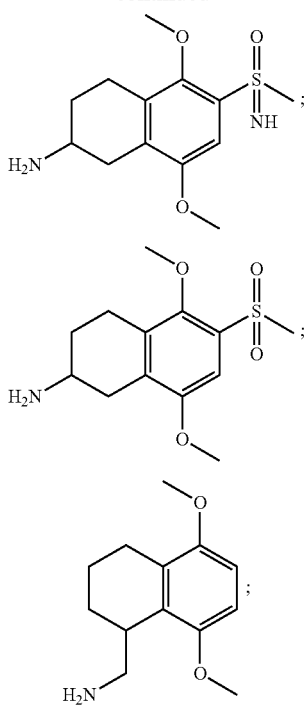

-continued

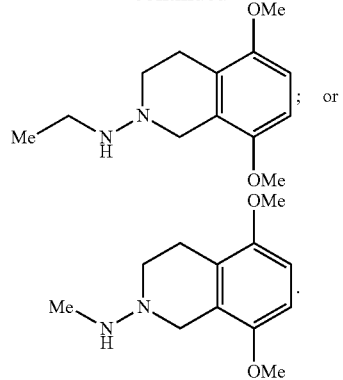

15. A pharmaceutical composition, comprising a compound of claim 1 and a pharmaceutically acceptable excipient.

16. A method of treating a mental health disease or disorder, the method comprising administering a therapeutically effective amount of the composition of claim 15.

17. A pharmaceutical composition, comprising a compound of claim 4 and a pharmaceutically acceptable excipient.

18. A method of treating a mental health disease or disorder, the method comprising administering a therapeutically effective amount of the composition of claim 17.

* * * * *